United States Patent
Redko et al.

(10) Patent No.: US 7,288,941 B2
(45) Date of Patent: Oct. 30, 2007

(54) METHOD AND APPARATUS FOR MEASURING CONDUCTIVITY OF POWDER MATERIALS USING EDDY CURRENTS

(75) Inventors: Volodymyr Redko, Coral Springs, FL (US); Volodymyr Khandetskyy, Dnipropetrovsk (UA); Peter Novak, Ft. Lauderdale, FL (US); Elena Shembel, Coral Springs, FL (US); Satoshi Kohara, Kanagawa (JP)

(73) Assignee: Enerize Corporation

( * ) Notice: Subject to any disclaimer, the term of this patent is extended or adjusted under 35 U.S.C. 154(b) by 0 days.

(21) Appl. No.: 11/244,796

(22) Filed: Oct. 6, 2005

(65) Prior Publication Data

US 2006/0127267 A1    Jun. 15, 2006

Related U.S. Application Data

(60) Provisional application No. 60/616,380, filed on Oct. 6, 2004.

(51) Int. Cl.
G01N 27/00    (2006.01)
G01R 33/14    (2006.01)
G01R 27/00    (2006.01)

(52) U.S. Cl. ........................ 324/450; 324/222; 324/663

(58) Field of Classification Search ................ 324/450, 324/222, 663
See application file for complete search history.

(56) References Cited

U.S. PATENT DOCUMENTS 4,986,946 A * 1/1991 Parish ........................ 264/104
5,343,150 A * 8/1994 Nakahata et al. ............ 324/316
5,442,298 A * 8/1995 Chang ........................ 324/724
5,451,882 A * 9/1995 Wakino et al. .............. 324/663
6,051,970 A * 4/2000 Hutchings .................... 324/204

FOREIGN PATENT DOCUMENTS

FR    2672687 A1 *  8/1992

* cited by examiner

Primary Examiner—Walter Benson
Assistant Examiner—John Zhu
(74) Attorney, Agent, or Firm—Akerman Senterfitt

(57) ABSTRACT

A method and related apparatus for non-contact measurement of electrical conductivity of powder-like materials using eddy currents includes the steps of placing a powder to be measured in a hollow dielectric sampling container, the sampling container disposed and freely axially moving within an outer dielectric housing. An eddy-current sensor including a winding is arranged on an outside surface of the housing. Current is forced in the winding to excite the powder to generate eddy currents. The introduced active resistance is measured at the eddy-current sensor and an electrical conductivity of the powder is determined using the measured active resistance. The powder is preferably vibration compacted and the density and electrical conductivity determined at a plurality of stages during the vibration compacting step.

12 Claims, 8 Drawing Sheets

METHOD AND APPARATUS FOR MEASURING CONDUCTIVITY OF POWDER MATERIALS USING EDDY CURRENTS

CROSS-REFERENCE TO RELATED APPLICATIONS

This application incorporates by reference in its entirety and claims priority to Provisional Application No. 60/616,380 filed on Oct. 6, 2004.

FIELD OF THE INVENTION

The invention relates to the methods and apparatus for measuring the electrical properties of non-metallic powder-like materials using eddy currents.

BACKGROUND OF THE INVENTION

The electrical conductance of electrode and electrolyte materials can be critical parameter for a variety of devices, including lithium-based batteries, supercapacitors and certain fuel cells. Contact measurements fail to accurately determine this parameter for powder-like materials as the electrical resistance of the grains chain to the current that flows in succession through them is mainly determined by the contact resistances in places the grains contact each other, while these resistances substantially exceed their inner resistances. This is explained by two reasons. First, the contacting grains, when the powder is of minor density (within the operating range of the powder densities being used for electrode coats of the chemical power sources) obtained by vibration compacting, have relatively small areas of contact there among. Second, the surface resistance of the powder grains is as a rule substantially higher of the volume resistance. This is explained by a lower concentration of free charge carriers on the surface of the grains and by their lower mobility, by forming, due to the chemical interaction with the atmosphere, of various types of insulating films, surface layers, inclusions.

The eddy-current method for measuring electrical conductivity is well known and relatively straightforward non-contact method for characterizing the electrical conductivity of continuous media, such as metals and semiconductors. The theory of interaction between the eddy magnetic fields and homogenous conducting materials has been adequately developed, and instruments for electrical conductivity measurement have been produced. However, layers comprising a variety of devices, including lithium-based batteries generally utilize powder like materials, rather than continuous media. Accordingly, the eddy-current measuring method of powder conductivity and the eddy-current method of conductivity measurement for continuous media are necessarily significantly different, as described below.

In contrast to eddy currents in continuous materials, the eddy currents in powders are mainly locked within each separate particle (each grain) of the powder. The active resistance introduced into the eddy current sensor and formed due to the loss of the field source power as a result of the eddy current flowing through the conducting medium is formed in the case of the powder as a sum of the joule losses in each grain.

The density of the eddy current induced by the field in each powder grain, according to the Ohm's law equals:

$$j = \sigma_0 E, \tag{a}$$

where $\sigma_0$ is the specific electrical conductance of the grain material, E is the electric field intensity in the place of the grain location.

The electric field intensity E is related to the magnetic field intensity of sensor H through the Maxwell's equation:

$$rotE = -\mu\mu_0 \frac{\partial H}{\partial t}, \tag{b}$$

where $\mu$ is the magnetic permeability of the medium, $\mu_0 = 4\pi \cdot 10^{-7} H \cdot m^{-1}$ – magnetic constant.

By introducing vector—potential A: $rotA = -\mu\mu_0 H$ for the harmonic field of the sensor in the form of a cylindrical inductance coil the following is obtained:

$$\dot{E} = -i\omega W \dot{A}, \tag{c}$$

where $i = \sqrt{-1}$, $\omega$ – angular frequency, W – number of turns in the sensor.

In a homogeneous magnetic field of a cylindrical inductance coil, the filed intensity H being identical at all points of the inner space of the coil, the eddy current density j induced in the grains of the powder filling this space will be identical too. This follows from equations (a)-(c).

The power of active losses in a single grain of the powder equals:

$$P_n = I_n^2 R_n, \tag{d}$$

where $I_n$ and $R_n$—respectively is the eddy current flowing along a circular trajectory in the grain, and the ohmic resistance of the grain material.

A case is now considered where the inner space of height h in a cylindrical inductance coil (an eddy-current sensor) is filled with powder grains of identical size shaped as globes of diameter D and densely arranged relatively to each other.

Then the total power of the active (Joule) losses for all the grains equals $$P_\Sigma = N_1 \sigma_0 E^2 Sl, \tag{e}$$

where $N_1$ is the number of grains in the inner space of the sensor, S and l correspondingly is the cross-section and length of the eddy current pipe in the grain.

The number of grains $N_1$ is now determined in the first approximation as the relation between the volume of the inner space of the sensor densely filled with the grains and the volume of one grain:

$$N_1 = \frac{3}{2} \frac{D_1^2 h}{D^3}, \tag{f}$$

where $D_1$ is the inner diameter of the cylindrical inductance coil, h—the height of its inner space, D—grain diameter.

FIG. 1(a) shows the arrangement of the current trajectories in a grain that is found in a homogeneous eddy magnetic field of intensity H. At high frequencies the eddy currents are pressed to the surface of the grains. This phenomenon is known as the skin-effect. The radius of the average (resultant) eddy current pipe in a grain are now determined. To this end, N eddy current pipes found within the region y>0 is considered as shown in FIG. 1(b) which defines coordinates of eddy current pipes. The width of each pipe equals D/2N. The coordinates of the first pipe along the Y-axis: 0, D/2N; of the second pipe D/2N, 2D/2N; of the third pipe 2D/2N, 3D/2N; and so on. The radius of the first eddy current pipe: $R_1 = D/2$. The radius of the second pipe is found from the equation of a circle: $X^2 + y^2 = D^2/4$; in this case $R_2 = (D^2/4 - D^2/4N^2)^{1/2}$. The radius of the third pipe: $R_3 = (D^2/4 - 4D^2/4N^2)^{1/2}$; of the fourth pipe: $R_4 = (D^2/4 - 9D^2/4N^2)^{1/2}$, and so on. The radius of the last N-th pipe $R_N = [D^2/4 - (N-1)^2 D^2/4N^2]^{1/2}$. Hence the average radius of an eddy current pipe in a powder grain of globular shape equals:

$$R_{av} = \frac{1}{N} \left[ \frac{D}{2} + \frac{D}{2N}(N^2 - 1)^{1/2} + \frac{D}{2N}(N^2 - 4)^{1/2} + \frac{D}{2N}(N^2 - 9)^{1/2} + \ldots + \frac{D}{2N}(2N - 1)^{1/2} \right],$$

or in a general form $$R_{av} = \frac{D}{2N^2} \sum_{n=0}^{N-1} (N^2 - n^2)^{1/2}. \quad (g)$$

Hence the average length of an eddy current pipe $l = 2\pi R_{av}$, while the pipe cross-section is assumed to be equal $S = \pi d_0^2/4$. The total number of such pipes in a grain is $D/d_0$.

$$P_\Sigma = \frac{3\pi^2 D_1 h d_0 \sigma_0 E^2}{8D} \cdot \frac{1}{N^2} \sum_{n=0}^{N-1} (N^2 - n^2)^{1/2}. \quad (h)$$

$$P_\Sigma = \frac{3.05 D_1^2 h d_0 \sigma_0 E^2}{D}. \quad (i)$$

As can be seen from equations (h) and (i), the total sensor field power of the Joule losses in the powder grains that densely fill the inner space of the sensor is a function of the grains diameter.

The influence of the powder density is now considered. The powder density $\rho_p$ equals:

$$\rho_p = \frac{M}{V} = \frac{N_\rho \cdot \rho_0 V_0}{V} = N_\rho \cdot \rho_0 \cdot \frac{2D^3}{3D_1^2 h}, \quad (j)$$

where M is the powder mass in the inner space of the sensor of volume V, $N_{92}$ is the number of the powder grains at the specified density, $\rho_0$—grain density, $V_0$—grain volume, D—grain diameter, $D_1$—inner diameter of the cylindrical inductance coil (of the eddy-current sensor), h—height of the sensor inner space of volume V.

Assuming, similar to (i) N=10, (see FIG. 1(b), the expression (e) for the total power of the Joule losses the following is obtained:

$$P_\Sigma = N_\rho \cdot 0.206 \pi^2 D d_0^2 \sigma_0 E^2. \quad (k)$$

Determining $N_\rho$ from (j) and substituting it into (k), results in:

$$P_\Sigma = \frac{3.05 D_1^2 h d_0 \rho_p \sigma_0 E^2}{D \rho_0}. \quad (l)$$

Taking into account that the power of the Joule losses of the sensor field in a conducting medium when eddy currents flow therein, is proportional to the active resistance introduced into the sensor, the following is obtained:

$$R_{ad}^{(p)} = k q \rho_p \sigma_0, \quad (m)$$

where $R_{ad}^{(p)}$ is the introduced into the sensor active resistance formed during the non-contact control of the powder of density $\rho_p$; $\sigma_0$ is the specific electric conductance of the powder grain; k is the proportionality coefficient, $q = 3D_1^2 h d_0 E^2 / D \rho_0$.

Thus, for the given powder with fixed values of $\sigma_0$, $\rho_0$ and D the value of the introduced active resistance of the sensor is proportional to the powder density $\rho_p$.

The theory of interaction between the axi-symmetrical eddy magnetic field of a cylindrical inductance coil (pass-through eddy-current sensor) and the conducting medium filling the inner space of a sensor has been developed for continuous homogeneous media.

For such a homogeneous medium let us take as an elementary the eddy current pipe of section $d_0$ and diameter $D_0 = 2R_{av} = 0.826D$ (Eqs. g-i). The number of such elementary pipes in the medium filling the inner space of the sensor of height h equals:

$$N_S = \frac{D_1^2 h}{0.682 D^2 d_0}. \quad (n)$$

The power of the Joule losses in the medium is determined as follows:

$$P_\Sigma^{(S)} = \frac{2.98 \cdot D_1^2 h d_0 \sigma E^2}{D}, \quad (o)$$

where $\sigma$ is the specific electric conductance of a continuous medium.

Taking into account that the introduced active resistance is $R_{ad}^{(S)} = k P_\Sigma^{(S)}$, from the condition of equality of the introduced active resistances for a continuous medium and for the powder: $R_{ad}^{(P)} = R_{ad}^{(S)}$, on the basis of equations (l) and (o) the following is obtained:

$$\frac{3.05 D_1^2 h d_0 \rho_p \sigma_0 E^2}{D \rho_0} = \frac{2.98 D_1^2 h d_0 \sigma E^2}{D}; \quad (p)$$

or $$\frac{\sigma_0}{\rho_0} = 0.977 \frac{\sigma}{\rho_p}. \quad (q)$$

Taking into account that during the vibration compacting the ratio between the powder grain density and the powder density $\rho_0/\rho_p$ is always above unity, the specific conductance of the powder grains always exceeds the value of the equivalent conductance of continuous homogeneous medium.

The equivalent conductance value can be calculated according to the measured value of the introduced active resistance for powder $R_{ad}^{(P)}$ using the tables contained. An example of such calculation is given in the description of the present invention.

It should be noted that equation (q) does not include the grain diameter D.

The ratio between the specific electric conductance of the powder grain $\sigma_0$ and the grain density $\rho_0$ is now designated by symbol $\gamma$:

$$\gamma = \frac{\sigma_0}{\rho_0}, \qquad (r)$$

and termed the reduced conductance of the powder grains.

At constant $\rho_0$ value $\gamma$ is proportional to $\sigma_0$—the specific electric conductance of the powder grains.

The powder grains are porous. The higher is the porosity, the less is the density of the grains and higher $\gamma$. In electrolyte applications for batteries, the electrolyte penetrates into the pores of the coat thus increasing the total surface area of the contact between the electrode coat and the electrolyte (the active surface area of the coat). Therefore, powders featuring a substantial electric conductivity per grain density unit (high $\gamma$) are of great value for electrode coats of chemical power sources.

The cathode coat of chemical power sources is of composite structure comprised of the basic powder-like material whose grains feature ionic conductivity, such as spinels $LiMn_2O_4$ or $MnO_2$, and of fillers, such as graphite powders and soot. The mixture of such powders in a liquid medium of an organic binder is thoroughly mixed in order to obtain a homogenous mass. In such case a high uniformity of the obtained material, that is the uniformity of the spatial distribution of grains of all the three types of powders is a function of the closeness of the density values of their grains. The lightest component of the mix is soot. Therefore of critical importance is to adequately select the powders of the spinel and graphite of low density of the grains and (naturally) of grains with a high specific conductance, that is, with a high $\gamma$ value.

The directly proportional dependence between the equivalent $\sigma$ and density $\rho_p$ for the given powder with the fixed $\sigma_0$ and $\rho_0$ values can be disrupted due to the interaction of the magnetic fields of the eddy currents in adjacent grains and the shifting currents among the grains.

The highest effect of this can be observed at maximum compaction when the powder grains are found at the maximum distance from each other.

The intensity of the displacement current is proportional to frequency $\omega$ and capacitance C among the particles that increases during the powder compaction.

The mutual inductance of the two circular currents with identical radii $R_{av}$ (Eq. g), that are flowing in adjacent powder grains can be calculated using the following formula:

$$M = \frac{\pi}{16}\mu_0\left(\frac{d}{a}\right)\xi\left[\frac{b}{y} - 1 + \right. \qquad (s)$$

-continued
$$\frac{\xi^2}{2}\left(1 - \frac{3}{2}\eta^2 + \frac{1}{2\eta^3}\right) - \frac{5}{8}\xi^4\left(1 - 5\eta^2 + \frac{35}{8}\eta^4 - \frac{3}{8}\cdot\frac{1}{\eta^5}\right) +$$
$$\frac{35}{32}\xi^6\left(1 - \frac{21}{2}\eta^2 + \frac{189}{8}\eta^4 - \frac{231}{16}\eta^6 + \frac{5}{16\eta^7}\right) + \ldots \bigg],$$

where $d=2R_{av}$ is the circular trajectory diameter of the eddy current; $a=D/20$ (similar to i), where D is the powder grain diameter; y—distance between the grain centers; $b=\sqrt{y^2+a^2}$, $\xi=d/2$, $\eta=y/b$.

The values of $M/M_0$ calculated according to (s) where $M_0=M(y=D)$, that is when two grains are closely arranged, depending on the least distance between the lateral surfaces of the grains x=y−D are given in Table A.

TABLE A

| $M/M_0$ | x/D |
|---------|-----|
| 1       | 0   |
| 0.906   | 0.1 |
| 0.835   | 0.2 |
| 0.712   | 0.4 |
| 0.626   | 0.6 |
| 0.554   | 0.8 |
| 0.50    | 1.0 |

It follows from Table A that at x=D the mutual inductance between the eddy currents induced in the adjacent powder grains becomes twice lower.

When there is no directly proportional relationship between $\sigma$ and $\rho_p$ due to the interaction of the magnetic fields of the grain eddy currents and to the presence of the displacement currents among the grains it is necessary to approximate the equivalent electrical conductance $\sigma$ as a function of density $\rho_p$ using a polynomial function of moderate order with a subsequent segregation of the linear term whose coefficient represents a derivative of the equivalent electrical conductance per powder density and is equal to the specific powder grains conductance reduced to their unit density.

SUMMARY OF THE INVENTION

A method and related apparatus for non-contact measurement of electrical conductivity of powder-like materials using eddy currents includes the steps of A method for non-contact measurement of electrical conductivity of powder-like materials using eddy currents comprises the steps of placing a powder to be measured in a sampling container comprising a hollow dielectric material, the sampling container disposed and freely axially moving within an outer dielectric housing. An eddy-current sensor comprising a winding is arranged on an outside surface of the housing. Current is forced in the winding to excite the powder to generate eddy currents. The introduced active resistance is measuring at the eddy-current sensor, and an electrical conductivity of the powder is determined using the active resistance.

The method can further comprise the step of determining an axial movement of the sampling container relative to the housing, and correcting the active resistance for the axial movement. The axial movement is generally determined using a capacitive measurement.

In a preferred embodiment, the method further comprises the step of measuring a density of the powder: in this embodiment, vibration compacting of said powder is preferably performed, and the determining of electrical conductivity and measuring of density recorded at a plurality of stages during the vibration compacting step. The vibration compacting step can comprise powering an electromagnet disposed under a bottom of the sampling container using a series of current pulses.

The method can include the step of disposing a hollow thin-walled dielectric cylinder whose lateral surface includes an electrically conductive layer thereon inside the sampling container on top of the powder. in this embodiment, the method can include the step of measuring a level of the powder in said sampling container during the vibration compacting step based on a capacitance between a pair of spaced apart electrical conductors disposed on an outer surface of the housing and the electrically conductive layer on the thin-walled dielectric cylinder.

A minimum bulk density and a maximum bulk density are generally determined during the vibration compacting step. The method can include the step of determining frequency band limits for an operating frequency of the eddy current sensor using the minimum bulk density and the maximum bulk density, and determining the operating frequency within the band limits according to a maximum Q-factor of the eddy current sensor.

An eddy current sensing apparatus for non-contact measurement of electrical conductivity of powder-like materials, comprises an outer dielectric housing having at least a first pair of electrically isolated electrically conductive wafers disposed on a lower outer surface thereof and a second pair of electrically isolated electrically conductive wafers disposed on a upper outer surface thereof, a sampling container comprising a hollow dielectric material for holding a powder sample to be measured, the sampling container having a continuous electrically conductive layer disposed on an outside surface of a lower portion thereof. The term "wafer" is used herein to indicate an article that has an area that significantly exceeds its thickness. The sampling container is disposed within and freely axially moving within said housing generally in an air gap region.

A hollow dielectric mass is provided, a lateral surface the dielectric mass having an electrically conductive coating thereon. The dielectric mass is disposed inside the sampling container on the powder sample. An eddy-current sensor comprising a winding is arranged on an outside surface of the housing in a middle portion thereof. A power supply forces current in said winding to excite said powder sample to generate eddy currents which are detected and measured as introduced active resistance by the eddy-current sensor. The first pair of electrically isolated electrically conductive wafers together with said continuous electrically conductive layer disposed on an outside surface of the sampling container provides capacitance data for determining a weight of said powder sample, and the second first pair of electrically isolated electrically conductive wafers together with the electrically conductive coating on the dielectric mass thereon provides capacitance data for measuring a powder level of the powder sample.

The apparatus preferably includes a vibration device for compacting the powder sample, such as a flask including an electromagnet, and a system of springs whose upper base is comprised of a magnetic wafer affixed to the springs, wherein a bottom of the flask is placed on the magnetic wafer, a mechanism for fixing the flask bottom on the magnetic wafer, and a current pulse series generator that powers the electromagnet, wherein the springs attach to a bottom of the sampling container. The system of springs can provide a weight of the powder, wherein the continuous electrically conductive layer is disposed on an outside surface of a lower portion of the sampling container is galvanically linked with the system of springs.

BRIEF DESCRIPTION OF THE DRAWINGS

There is shown in the drawings embodiments which are presently preferred, it being understood, however, that the invention can be embodied in other forms without departing from the spirit or essential attributes thereof.

DETAILED DESCRIPTION OF THE INVENTION

The invention includes methods and apparatus for measuring the electrical conductance of powders using an eddy-current method. The eddy current method is inherently a non-contact method which does not suffer from measurement error resulting from contact resistance which plagues direct-contact measurement methods. In particular, the invention can be used to measure the electrical conductivity of non-metallic powders, and can provide conductance values across a range of powder density values.

Eddy current theory is well known and is briefly repeated only for completeness herein. When a simple coil is placed in close proximity to an electrically conductive surface and an AC current is forced to flow in the coil, the resulting magnetic field generated by the coil will induce circulating (eddy) currents in that surface. The magnitude and phase of the eddy currents will affect the loading on the coil and thus its impedance.

Figure 1A:
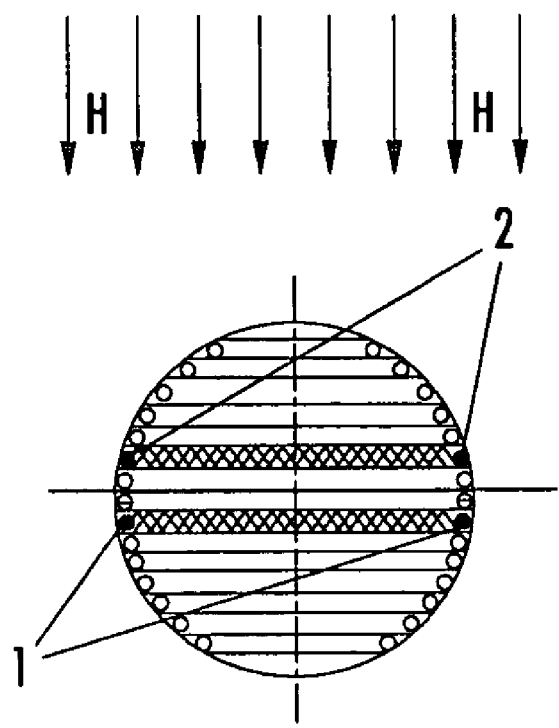
FIG. 1(a) shows the arrangement of the current trajectories in a grain that is found in a homogeneous eddy magnetic field of intensity H. At high frequencies the eddy currents are pressed to the surface of the grains.
Figure 1B:
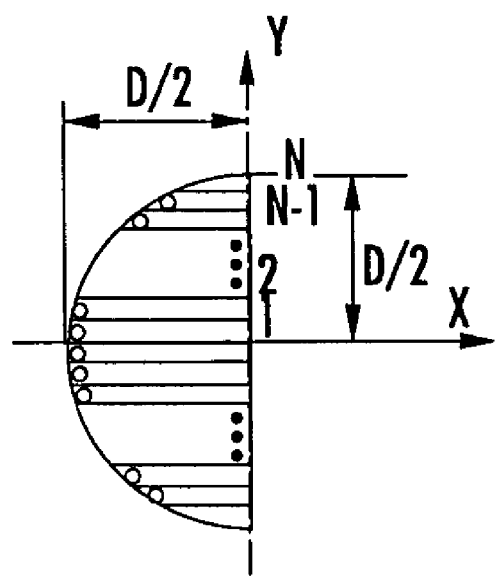
FIG. 1(b) defines coordinates of eddy current pipes.
Figure 2:
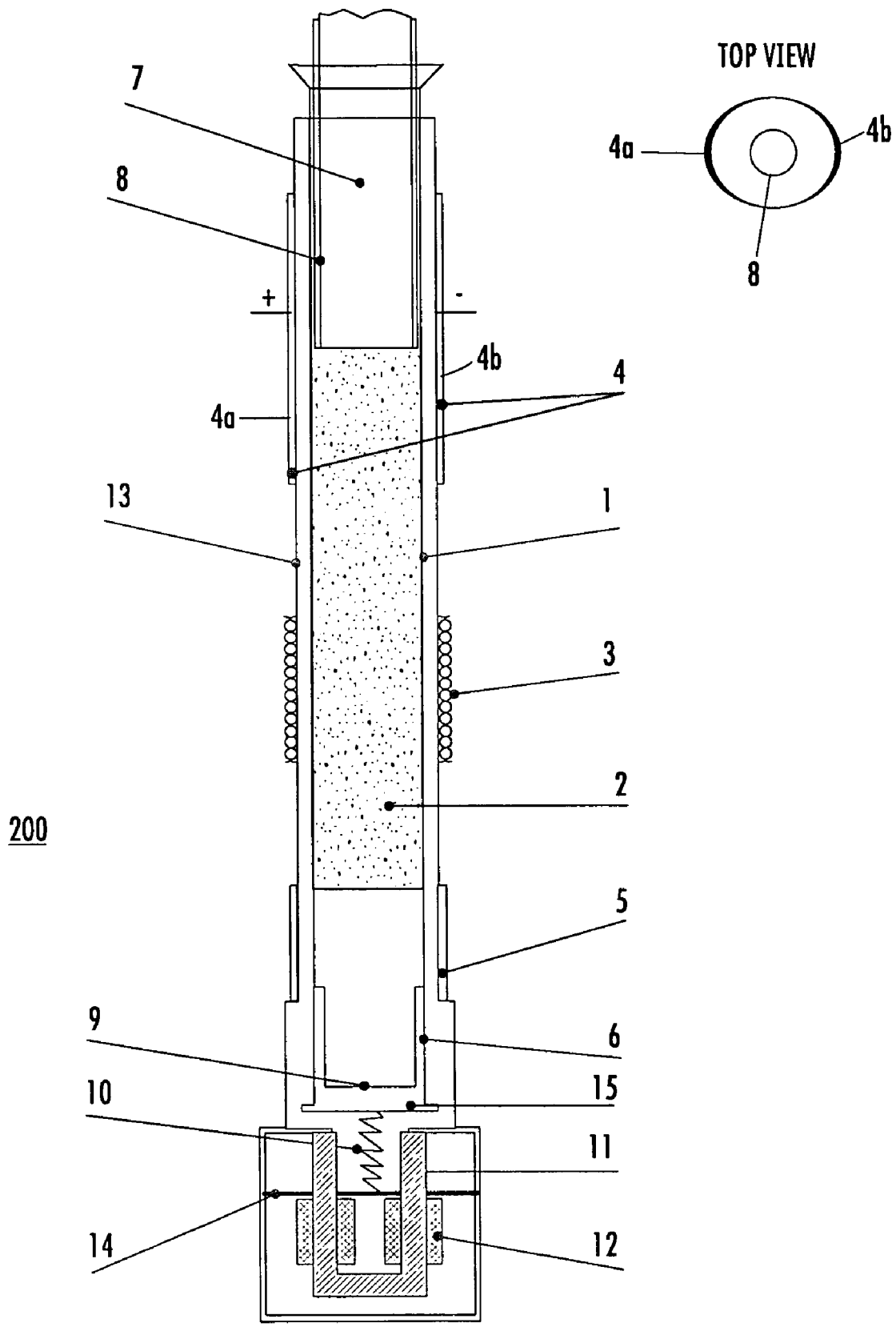
FIG. 2 shows an apparatus for measuring the electrical conductivity of powders using eddy currents, according to an embodiment of the invention.
Figure 3:
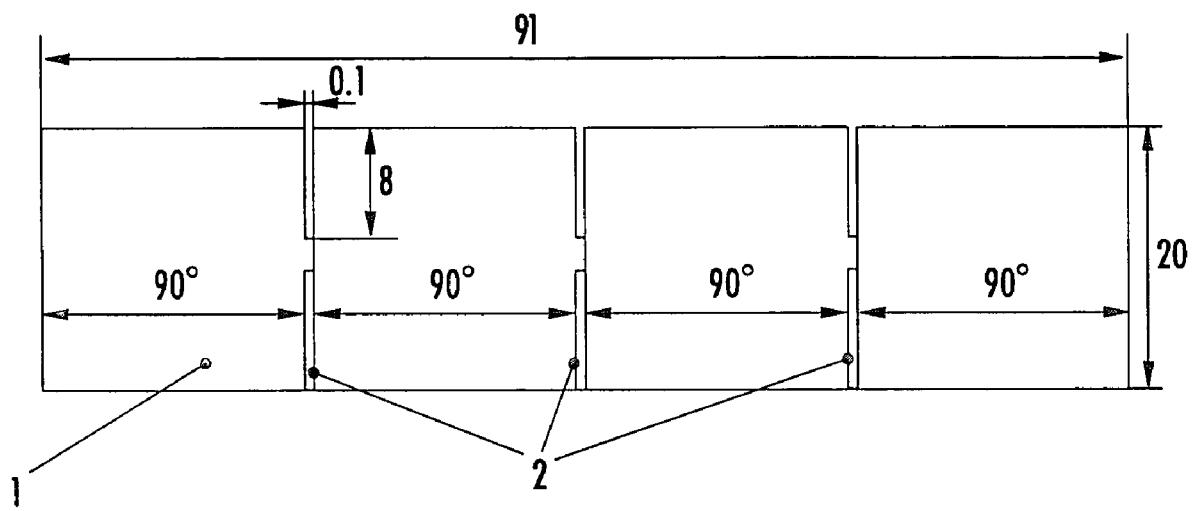
FIG. 3 shows a preferred design for the outer electrode of the weight measuring capacitor, according to an embodiment of the invention.

Referring to FIG. 2, an apparatus 200 for measuring the electrical conductivity of powders is shown. Apparatus 200 includes a dielectric sampler 1 which is sized to fit within a dielectric housing 13. The sampler 1 and housing 13 are preferably cylindrically shaped as shown in FIG. 2, and made from a material such as a fiberglass laminate, although other cross sectional shapes and other dielectric materials are possible. The inner diameter of the cylindrical housing 13 is preferably several millimeters in excess of the outer diameter of the sampler 1. In one exemplary embodiment, the outer diameter of the sampler $D_{out.\ samp.}$ can be 24 mm while the inner diameter of the housing $D_{inn.\ cas.}$ can be 27 mm. When such a sampler 1 and housing 13 are positioned coaxially the gap between their walls equals 1.5 mm. This allows avoiding any substantial friction between the sampler 1 and the casing 13 during vibration. The total height of the sampler can be about 190 mm. An inductance coil 3 functioning as a pass-through eddy-current sensor is wound on the outer surface of the housing 13, preferably in the vicinity of its middle section as shown in FIG. 2.

To determine the level of powder 2 in the sampler 1, on the top thereof, a hollow thin-wall cylinder 7 made of a dielectric material is placed whose lateral surface is adhesively lined with a continuous metallic foil 8. Powder level measurement permits determination of the powder volume being tested since the cross sectional area of the powder defined by the inner dimensions of sampler 1 is a known constant. The distance between the foil surface and the inner surface of the sampler 1 is preferably about 0.1-0.2 mm. On the outer surface of the housing 13, in its upper part, substantially symmetrically to the axis of housing 13, two spaced apart conductors 4a and 4b are arranged which together with conductor 8 form a capacitor.

The electric field of the outer electrodes 4a and 4b arranged in the recesses of the outer surface of housing 13 concentrates opposite sign charges on the foil surface, thus forming two series connected capacitors which allows measurement of the powder level in the sampler 1. If the axes of the sampler 1 and the housing 13 coincide then the capacitances of these capacitors are equal. Correspondingly, the capacity of an equivalent capacitor for measuring the powder level in the sampler equals half of the capacity of each of the formed capacitors.

In the initial position, immediately after charging the powder 2 into the sampler 1, the powder level is at its maximum while the capacitance of the equivalent level capacitor is minimal. After starting the powder compacting by mechanical vibration of the sampler the powder level starts getting reduced, the cylinder 7 installed on the powder 2 descends while the level condenser capacity increases linearly with the change of the level.

On the same outer surface of housing 13, but in its lower part, an outer cylindrical electrode 5 is disposed for determining the powder weight in the sampler. The other electrode of this capacitor 6 can comprise a metallic foil strip placed in a recess of the lateral surface of the sampler 1.

In order to reduce the influence of electrode 5 on measurements made by the eddy-current sensor 3, several thin slots are preferably formed both in the upper and lower parts of the body of electrode 5. For example, there can be four slots, 0.1 mm wide each, after each 90° along the contour. The total electrode width can be 20 mm, while each slot can be 8 mm long. The total surface area of the eight slots, each of 0.1 mm wide and 8 mm long, equals 6.4 mm$^2$, or less than 1% of the total surface area of the electrode. This exemplary embodiment is shown in FIG. 2. The slots in the lower part of the electrode 5 allow an increase in the degree of linearity of the capacitor formed by electrodes 5 and 6 which permits determination of the powder weight via the vertical shift of electrodes 5 and 6 relative to each other. Thus, the influence of the slots on the total capacity of the weight measuring capacitor can be insignificant.

The slots formed in the upper part of electrode 5 are in the area of the higher field intensity of the sensor winding 3. This substantially reduces the intensity of the eddy currents running along closed trajectories coaxial with the casing because they actually impede the way of these currents. Thus the influence of electrode 5 on the measurement provided by the eddy-current sensor 3 is reduced even more.

The second electrode 6 of the capacitor for weighing the powder sample can be comprised of metallic foil which can be glued to the sampler in its lateral surface recess so that the outer foil surface coincides with the lateral surface of the sampler beyond the recess. The strip width of the metallic foil 6 equals the width of the outer electrode of the capacitor formed by electrodes 5 and 6. The strip 6 is secured, such as using solder, to metal strip 9, such as formed from an aluminum alloy which forms the flask bottom. The thickness of metal strip 9 can be 2-3 mm. The weight of such a strip 9 is 2.44-3.66 g. At the center of metal strip 9 is a threaded hole into which a screw is screwed in and glued so that some part of it protrudes relative to the lower base of the metal strip 9.

In the lower part of housing 13 a vibration type flask powder compacting device is arranged containing a magnetic winding 12, an electromagnet 11, a system of springs 10, the upper base of which is formed by a plate 15 made of a magnetic metal, such as 2 mm thick magnetic steel. The electromagnet winding 11/12 is preferably powered by a pulse series generator (not shown).

The weight of plate 15 can be about 7 g. Plate 15 includes a threaded hole for screwing in a screw fixed in the bottom of the sampler 1. The base of the springs 10 is fixed below to this plate 15 by spot welding. The plate 15 includes lateral protrusions that come into respective slots in the casing thus precluding its turning in the horizontal plane. Thus, the sampler bottom is affixed to plate 15 with springs 10.

During vibration of the sampler 1 the powder becomes compressed lowering its level in the sampler. As a result, the dielectric cylinder 7 with the lateral side coated with electrode 8 and installed on top of the powder 2 being measured descends together with the powder while the capacity of the equivalent capacitor for measuring the powder level increases. The dependence between the capacity and the powder level is essentially linear. The cylinder 7 also compacts the powder on the top thus improving the density distribution uniformity throughout the powder height in the sampler 1.

During vibration the sampler 1 can become radially shifted relative to the fixed outer casing provided by housing 13. The radial shifting of the sampler 1 causes a change of the active resistance introduced into the eddy-current sensor 3 that if left uncompensated can cause significant errors in measuring the electrical conductance of the powder 2. The capacitance is preferably measured after each operating stage of the vibration device. As the sample powder weight is constant, the capacitance of the weight measuring capacitor will depend only on the radial shift of the sampler 1. Thus, through measurement of capacitance of the weight measuring capacitor, and including this capacitance in the determination of powder conductivity, radial shifting of the sampler 1 can be corrected out.

The distance between the upper end face of electrode 5 and the nearest to that end face coil of the eddy-current sensor winding 3 is preferably approximately to the diameter of the housing 13, that is approximately equal to the sensor winding diameter. The diameter of the winding wire typically does not exceed 1 mm, and is usually less. At the diameter distance from the end face of the inductance coil (solenoid) the field is by more than an order less than its value in the end face plane, therefore the eddy currents excited in electrode 5 can be neglected. The respective calculation is given in Example 1.

An exemplary method of using apparatus 200 is now described. A powder to be measured is charged into sampler 1. The sampler 1 is then installed in the cylindrical housing 13. Dielectric cylinder 7 is placed on the powder 2. Before the conductance measurement the powder 2 charged into the sampler 1 is weighed. For this purpose the springs 10 can be used. Due to the weight of the powder sample in the sampler 1, the sampler 1 moves downward while the inner electrode of the capacitor 6 fixed to the outer surface of the sampler 1 moves relative to fixed outer electrode 5 thus reducing the capacitance of the powder weight measuring capacitor. The dependence of this capacitance on weight is essentially linear.

For determining the powder level in the sampler 1, on top of the powder, dielectric cylinder 7 includes inner electrode 8 while housing 13 provides its outer electrodes 4(a) and 4(b). The electric field of outer electrodes 4(a) and 4(b) disposed on surface of housing 13 is screened by the metallic foil electrode 8 forming a circuit comprised of two connected in series capacitors internally clad by the stretches of the foil that are opposite to the outer electrodes 4(a) and 4(b). On these stretches the opposite polarity charges are concentrated under the influence of the electric fields of outer electrodes 4(a) and 4(b). In the initial position, immediately after powder charging into the sampler 1, the powder level is at a maximum, while the capacitance of the equivalent level capacitor is at a minimum.

The powder density in the sampler 1 is then determined as the sample weight divided by its volume that is calculated according to the measured level value. A powder electrical conductivity value can be obtained after each compacting stage is accompanied by its corresponding density value. Thus, during the compacting procedure the electrical conductivity values and the respective density values are accumulated. In most cases, it is desired to record the electrical conductivity value achieved at maximum density. The electrical conductivity values can be approximated using the least-squares method as a function of the density. The approximation can be performed using a first degree polynomial. A powder conductivity versus powder density can thus be derived.

When placing the sampler 1 with the powder sample therein into the housing 13 the inner electrode 6 of the lower capacitor is shifted relative to the outer electrode 5 by a value $\Delta x$ in the vertical direction. The range of compression of spring 10 corresponds to the linear region of the Hooke's law of displacement where the spring's compression value or value of shift $\Delta x$ is proportional to the compression force. Thus the powder weight $P_x$ causes a proportional displacement of outer electrode 5 an amount $\Delta x$ relative to electrode 6, and a respective proportional capacitance change of the capacitor $\Delta C_x$.

With a 20 mm width of the outer electrode 5 and inner electrode 6, the maximum shift $\Delta x_m=20$ mm corresponds to the powder weight in the sampler $P_x=40$ g, that corresponds to the initial (preliminary to compacting) powder density $\rho=0.7$ g/cm$^3$. If the proportionality between the weight $P_x$ and shift $\Delta x$ begins to become distorted with the approach of the range boundary $\Delta x$ a correction can be effected in the sample weight calculation unit.

Since the distance between the electrodes 5 and 6 is generally at least about an order of magnitude less than the width of electrodes 5 and 6, the calculation of the condenser capacitance between electrodes 5 and 6 can be calculated using a formula that determines the capacitance per length unit between the infinitely long cylindrical casings of circular cross-section. The respective calculation is shown in Example 2.

In such case the condenser capacitance between electrodes 5 and 6 for powder weight measuring changes from its maximum value Cpm=8.82 pF practically to zero at $\Delta x_m=20$ mm. Taking into regard that the dependence of the capacity $C_{pm}$ from $\Delta x$ is linear and that the spring shift takes place within the range of the Hook's law validity (F=-κ·$\Delta x$), the sensitivity of the weight measuring capacitor q=$C_{pm}$/P=0.22 pF/g, and is essentially constant within the whole change range of the condenser capacitance.

Additional Preferred Method Steps and Related Subject Matter

A more preferred method of using apparatus 200 is now described below. The preferred method includes selection for frequency band limits for frequency selection based on measured parameters of the powder and selection of the operating frequency within the band. A thin-walled cylindrically shaped sampler made of a dielectric with a powder charged therein is placed inside of a cylindrical housing (casing) having with the sampler a common axis of symmetry while maintaining an air clearance between the outer surface of the sampler and the inner surface of the casing. The winding of a parametric eddy current sensor is positioned on the outer surface of the cylindrical casing in the middle part thereof. The frequency band limits for the selection of the eddy current sensor operating frequency are then determined by using the minimum bulk density and the maximum density achieved by vibration compacting. The operating frequency within the given band is then determined according to the maximum Q-factor of the eddy current sensor. Eddy currents in the powder grains are excited and introduced active resistance of the parametric eddy current sensor measured at different powder densities during the vibration compacting process. The powder weight in the sampler is measured against the electrical capacitance value between the closed metallic wafers of the weight capacitor, one of which being placed on the casing in the lower part thereof while the other being placed on the outer surface of the sampler. The powder is compacted in the sample by vibrating the sampler using an electromagnet placed under the bottom of the sampler whose winding is powered by series of current pulses. A hollow thin-walled cylinder whose lateral surface is coated with a metallic foil glued thereto is then installed in the sampler top onto the powder. The powder level in the sampler during the vibration compaction process is then measured, according the electrical capacitance change of the capacitor formed by the two metallic wafers placed on the cylindrical surface of the casing in its upper part, and the lateral surface of the cylinder placed on the top on the powder surface in the sampler. The error of measuring the active introduced resistance of the eddy current sensor is then corrected that is formed during the radial shift of the sampler inside of the casing within the clearance during the vibration, using the capacitance values of the weight capacitor measured during the vibration process. According the values of the introduced active resistance of the eddy current sensor, the electrical conductivity equivalent to the powder is determined according to the criterion of the introduced active resistance of the continuous homogeneous medium (of equivalent electrical conductivity) at various values of the powder density. Finally, the relationship between the equivalent electrical conductivity and density is approximated by a polynom that is not higher of the third degree with a subsequent selection of the linear term whose coefficient that equals the derivative of the equivalent electrical conductivity relative to the powder density characterizes the specific electrical conductance of the powder grains reduced to the density unit of the grains.

The lower limit of the frequency band is preferably selected at a frequency at which the difference between the values that are inverse of the Q-factors of the sensor with the powder having the minimal bulk density and of the sensor without the powder exceeds $5 \cdot 10^{-5}$, and the upper limit of the frequency band is selected as a frequency at which the derivative of the introduced active resistance relative to the frequency for the sensor with the powder of maximum density reached during the vibration compacting changes its sign.

Preliminary to charging the powder into the sampler, calibration is preferably carried out of the weighing mechanism comprising a system of springs and a capacitor for weight measuring, at which the installation on the system of springs of the sampler without the powder but with a hollow cylinder causes the closed metallic wafer fixed on the sampler surface to be placed just opposite the outer wafer of the weight measuring capacitor, the wafer being located on the shell and having the same width that the wafer on the sampler. After weighing, the generator of a series of pulses is preferably switched on that sets vibration conditions. A parallel analogue-to-digital conversion of information that characterizes the capacitance values of the capacitors for measuring the level and the weight of the powder in the sampler, as well as the value of the relative introduced active resistance of the eddy current transducer is preferably performed, information is then transmitted in the digital form into a specialized microprocessor computer, the computer determines the sample volume, weight, the equivalent electrical conductivity of the powder, correcting action according to the capacitance change of the capacitor for weight measuring is determined, the correcting action being used in determining the equivalent electrical conductivity of the powder in the process of its vibration compacting.

The procedures for determining the sample volume, the equivalent electrical conductivity, and formation of the correcting action can be synchronized, with realization of the mentioned procedures in each time interval between the series of the current pulses powering the winding of the electromagnet for vibration compacting. The sample weight measured initially preliminary to powder compacting can be stored, with the powder density in the sampler determined by dividing the stored sample weight by its volume that is changing during the compacting process, with a synchronization of the procedure for determining the powder density with the procedure for determining its equivalent electrical conductivity.

The maximum density value reached in the process of vibration compacting can be determined, the equivalent powder electrical conductivity corresponding to the maximum density, and indication of these values fixated, accumulation of the equivalent electrical conductivity values corresponding to various powder density values realized during the compacting process, approximation of the obtained pairs of the equivalent electrical conductivity and density values, selection of the linear term of the approximating polynom, and determination of the steepness of the selected linear relationship that characterizes the specific conductance of the powder grains reduced to the density unit of the grains, and its indication.

Additional Preferred Apparatus Components and Details and Related Subject Matter The system of springs 12 in the compacting device is also used for powder weighing in the sampler 1, with the foil layer on the lower part of the sampler 6 being galvanically linked with the springs. The wafers of the capacitor for measuring the powder level in the flask 15 can intimately mate with the outer surface of the housing 13, have essentially identical shape and dimensions, are be arranged symmetrically to each other, with the distance between the lower edge of the wafers 15 and the nearest turn of the eddy current sensor 3 being equal to the diameter of housing 13.

The diameter of the outer metallic shell on the surface of the hollow cylinder can be several tenths of a millimeter less than the inner diameter of the sampler 1, with the shell width being not less than the width of the outer wafers 4a and 4b located in the upper part of the housing 13. The width of the metallic foil strip 6 in the lower part of the sampler 1 can equal the width of the outer wafer of the capacitor for weight measuring 5, with the distance between the upper end face of the wafer and the sensor winding turn nearest to that end face being equal to the diameter of the housing 13. The wafers of the capacitors for measuring the level and the weight of the powder in the sampler 1, 4a and 4b and 5, respectively, can contain thin vertical apertures of identical width and length arranged at an identical angular distance therebetween, and beginning both from the lower and the upper end faces of the wafers, while the strip width of the continuous metal in the central part of the wafers is being selected so as to preserve the mechanical strength of the wafers.

The wafers of the capacitors for measuring the level and weight of the powder, as well as the winding of the eddy current sensor 3 can be located in the apertures of the housing 13 so that the thickness of the housing wall in the places of the wafer and winding location is not more than 1 mm. In addition, the width of the outer wafers of the capacitor for measuring the powder level 4a and 4b is determined taking into regard the maximum compressibility of the powder from the batch being studied during vibration compacting, while the lower end face of the metallic shell on the hollow cylinder during maximum compaction should not get below of the lower end face of the outer wafers. The number of current pulses in the series coming from the pulse generator into the electromagnet winding gets increased from series to series while the powder is being compacted.

Figure 4:
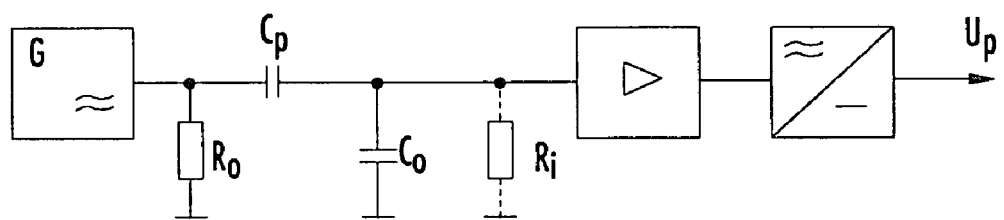
FIG. 4 shows a capacity measuring circuit of weight capacitor, according to an embodiment of the invention.

A circuit diagram of the capacity measuring unit of the weight determining capacitor formed by electrodes 5 and 6 is shown in FIG. 4. A generator of harmonic vibrations G, has an output resistance $(R_0)$=50 Ohm and an operating frequency f=10 kHz. Sensor $C_p$ and an additional capacitor $C_0$ form a capacitance divider whose output voltage on the capacitor terminals $C_0$, equals the following:

$$U_{c0} = U_{R0} \cdot \frac{C_p}{C_0 + C_p}, \quad (1)$$

where $U_{R0}$ is the voltage across output resistor $R_0$ of generator G. The maximum weight condenser capacity is Cpm=8.82 pF (see Example 2). Assume $C_0$=50·Cpm=441 pF. Then the value $C_p$ in the denominator (1) becomes negligible in comparison to $C_0$. Hence $$U_{c0} = \frac{C_p}{C_0} \cdot U_{R0}. \quad (2)$$

By specifying the generator output voltage value $U_{R0}$=10 V, the maximum value $C_p$=Cpm $U_{c0}$=0.2 V is obtained. The voltage of capacitor $C_0$ can be increased using an alternating current amplifier with an output resistance $R_i$=1 MOhm that is subsequently rectified using an active detector. The resistance of capacitor $C_0$ at the frequency f=10 kHz equals $X_{c0}$=36 kOhm. The amplifier input resistance $R_i$ is about 28 times higher of $X_{c0}$, therefore it is practically not shunted.

Structurally the capacitor $C_0$ and the alternating current amplifier are connected to the outer electrode 5 (see FIG. 2) of the capacitor for sample weight measuring. The output resistance of generator $R_0$ is switched in between the point of fixing the lower end of the spring 10 (see FIG. 2) and ground.

Figure 5:
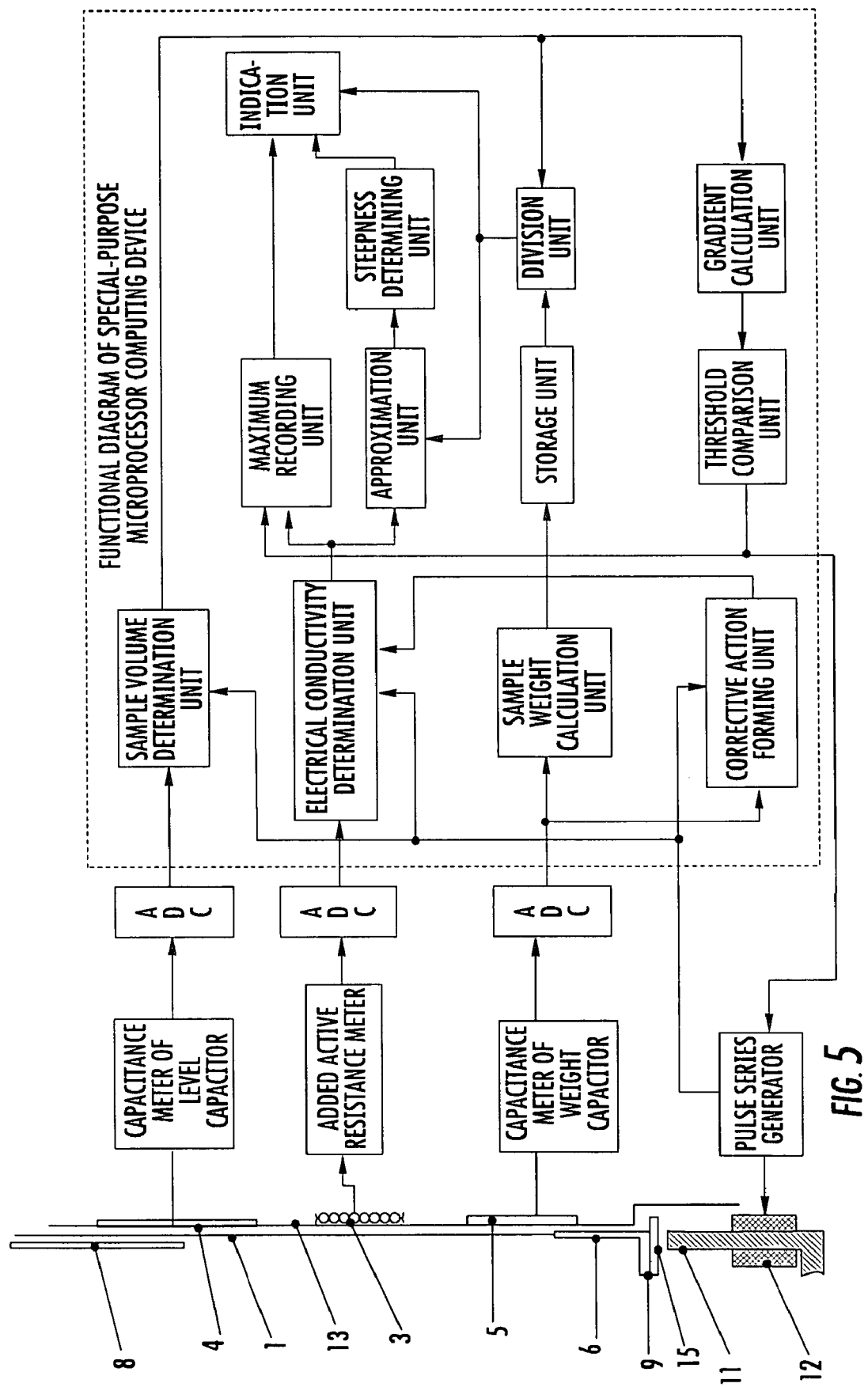
FIG. 5 shows functional scheme of a device, according to an embodiment of the invention.
Figure 6:
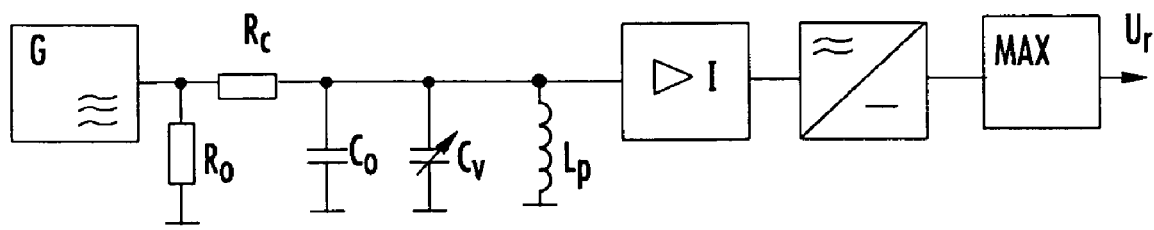
FIG. 6 shows an exemplary active added resistance measuring circuit, according to an embodiment of the invention.

The analog voltage from the measuring unit output of the weight condenser capacity formed by electrodes 5 and 6 is preferably converted to a digital form by an analog-to-digital converter and is directed to the input of the sample weight calculation unit in which a special-purpose microprocessor computing device is used as shown in FIG. 5. As the condenser capacitance is proportional to the sample weight the weight calculation unit performs a scaled conversion of the input code so that the output code will correspond to the sample weight of dozens of milligrams. This code is preferably stored.

As noted above, to measure the electrical conductance of the powder a pass-through type parametric eddy-current sensor 3 is used whose winding is arranged on the housing 13 near its middle part (see FIG. 2). The magnetic field of the sensor 3 generates eddy currents in the powder that travel along closed trajectories whose planes are perpendicular to the lateral surface of the sampler 1. Parallel to the eddy-current sensor winding 3 constant and variable capacity condensers are switched in forming a resonant circuit together with the eddy-current sensor 3. The circuit for measuring the input active resistance of the sensor is shown in FIG. 5. The circuit includes a generator of high-frequency harmonic voltage with an output resistance $R_0$, connected via a linkage element $R_c$ to the parallel oscillation circuit comprised of capacitors $C_0$, Cv and an eddy-current sensor Lp. The variable capacitor Cv serves to adjust the circuit to the resonance that is fixed according to the maximum output voltage. To the parallel resonant circuit a current amplifier with a high output resistance is switched whose output is connected to the input of the amplitude detector that is in its turn connected to the maximum generating circuit.

The resistance of the parallel circuit tuned in resonance with the frequency of generator G, is active and is equal to the equivalent resistance Re:

$$R_e = \frac{L_p}{(r_0 + r_{ad})(C_0 + C_v)}, \quad (3)$$

where $r_0$ is the active resistance of the eddy-current sensor winding, and $r_{ad}$ is the added active resistance due to the eddy currents passing through the powder. It has been found that a reduction of the sensor inductance Lp due to the negative added inductance is insignificant even for relatively well conducting graphite powders, and, besides, it is compensated by an increase of the parasite capacity of the coil under the environment influence.

It follows from expression (3) that $$r_0 + r_{ad} = \frac{L_p}{R_e C_\Sigma}, \quad (4)$$

where $C_\Sigma = C_0 + C_v$.

When there is no powder 2 in the sampler 1, $r_{ad}$=0, the resistance value of the linkage element formed either by a special resistor featuring a minimal reactive resistance at the measurement frequency, or a capacitor, or an inductance coil, is selected to be equivalent to the circuit resistance when there is no material to be measured, that is $R_c = R_{eo}$. Then $U_r = U_G/2$ (in the tract—current amplifier—amplitude detector the voltage is measured linearly). It can be written that $$r_0 = \frac{L_p}{R_{eo} C_\Sigma} = \frac{L_p}{R_c C_\Sigma}. \quad (5)$$

Then from (4) and (5) it follows $$r_{ad} = \frac{L_p}{C_\Sigma}\left(\frac{1}{R_e} - \frac{1}{R_c}\right) = \rho^2\left(\frac{1}{R_e} - \frac{1}{R_c}\right), \quad (6)$$

where ρ is the characteristic resistance of the circuit. While studying the measuring circuit in FIG. 5, it can be written $$U_r = k U_G \frac{R_e}{R_c + R_e}, \quad (7)$$

where k=const is the voltage conversion coefficient in the current amplifier—amplitude detector tract.

$$R_e = \frac{U_r \cdot R_c}{kU_G - U_r}. \quad (8)$$

Then

In this case $$\frac{r_{ad}}{\omega L_p} = \frac{1}{\omega R_c(C_0 + C_v)}\left(\frac{kU_G}{U_r} - 2\right). \quad (9)$$

Hence, knowing the value $U_r$ it is possible to determine the relative added active resistance of eddy-current sensor ($r_{ad}$). The analog voltage $U_r$ is preferably converted to a digital code and is entered into a specialized microprocessor computing device in which the electrical conductance determination unit calculates $r_{ad}/\omega L_p$ according to (9) (see FIG. 5.

Figure 7:
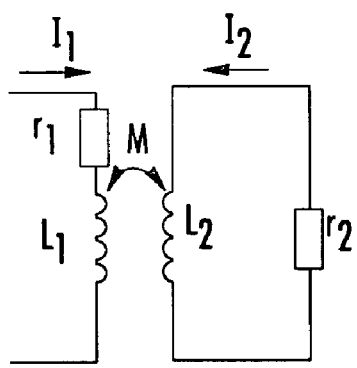
FIG. 7 shows an equivalent circuit showing the interaction between the fields of the sensor winding and the eddy currents.

When the axial line of the sampler with the powder is shifted relative to the axial line of the casing the value of the added active resistance of the eddy-current sensor changes. The eddy currents induced in the studied powder-like material by the magnetic field of the winding coils of the eddy-current sensor flow in the material along closed circular trajectories whose planes coincide with the coil planes of the sensor winding 3. The interaction of the eddy-current sensor field and the field of eddy currents can be described by an equivalent circuit shown in FIG. 7 In accordance with this equivalent circuit the added active resistance of the eddy-current sensor is determined by the following expression:

$$r_{ad} = \frac{X_m^2 r_2}{r_2^2 + X_2^2}, \quad (10)$$

where $r_{ad}$ is the added active resistance of the eddy-current sensor 3; $r_2$ is the total active resistance of the eddy current circular trajectories generated by the eddy-current sensor coils in the material being studied; $X_2$ is the inductive reactance of the eddy-current trajectories, $X_m = \omega M$ is the mutual induction resistance between the eddy-current circuits and the eddy-current sensor windings, $\omega$ is the angular frequency, and M is the mutual induction value.

In accordance with (10), the value of the added active resistance of the eddy-current sensor is determined by the characteristics of the material being studied and the mutual induction value between the coils of the eddy currents and the coils of the sensor winding.

Figure 8:
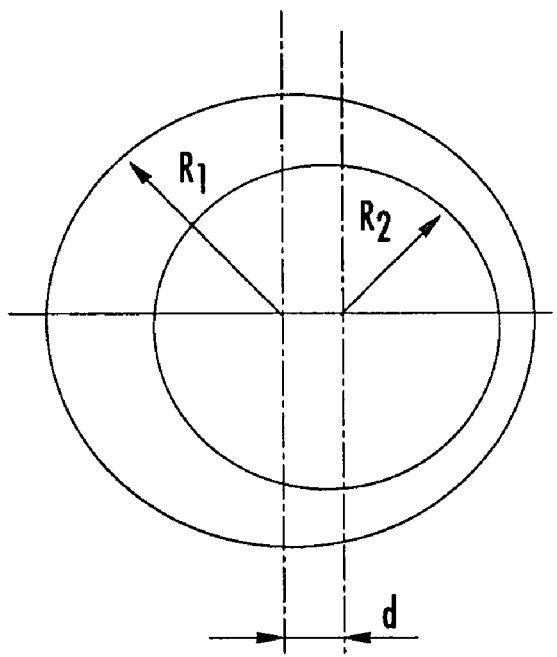
FIG. 8 shows a cross section of cylindrical casings, according to an embodiment of the invention.

When the axis of sampler 1 is shifted relative to the axis of the housing 13 by a value d (FIG. 8), the mutual induction M changes, changing in its turn the value of the added active resistance $r_{ad}$ of the eddy-current sensor 3, thus causing an error. The calculation of the value M changing by the shift d for one coil of the eddy-current sensor is given in Example 3.

When measuring the electrical conductivity of low-conductivity powders, in order to obtain a sizable reaction of the eddy-current sensor it is necessary to work in the range of dozens or more megacycles per second, with a sensor comprised of several coils. In order to upgrade the electrical conductivity measurement accuracy in this case it may become necessary to correct the changes of M when the sampler is shifted, and this is done using a capacitor for measuring the powder weight in the sampler.

As follows from FIG. 9 the changing curves of the square of self-inductance and of the weight measuring condenser capacity as a function of the shift value d of the axes of the sampler 1 and the casing 13 reduced to respective values at d=0, have a qualitatively similar shape. The output voltage of the weight condenser capacity meter converted to the digital form is fed to the inlet of the corrective action forming unit realized by means of a special-purpose microprocessor computing device. In this unit according to the value λ (see FIG. 9 the shift value d between the axes of the sampler and the housing is determined, whereupon value d is used for determining the corresponding value γ. The latter is transmitted to the electrical conductance determining unit where the value of the relative added active resistance $r_{ad}/\omega L_p$ (9) introduced into the eddy-current sensor is divided by the value γ. Thus, the correction is performed.

The corrected resistance value $r_{ad}/\omega L_p$ can be used for calculating the specific electrical conductance a using conventional formulas. The results of the experimental studies and of the electrical conductance calculation of graphite powders are shown in Example 6. The results of electrical conductance measurement of the same powders by a conventional contact method are shown in Example 8 as well as a comparison of the accuracy of the non-contact method according to the invention and contact measurements.

As noted above, the circuit for determining the volume occupied by the powder in the flask includes electrodes 4a and 4b disposed on the surface of housing 13 in its upper part. The distance between the lower end face of electrodes 4a and 4b and the coil of the eddy-current sensor winding 3 that is the nearest to this end face is specified to be equal to the housing diameter, that is to the diameter of the sensor winding. At a diameter distance from the coil end face the field is approximately by an order less of its value in the end face plane. The respective calculation is shown in the text of Example 1.

The study of the influence of sampler shifts in the radial direction during vibration on the level measuring condenser capacitance is illustrated by Example 4. The calculations demonstrate that this influence is insignificant.

The height of electrode 4a and 4b arranged on the housing 13 is calculated taking into regard the maximum volume of the powder in the sampler and the degree of its compression achieved during the experiments held (see Example 5).

The calculations provided show that when the maximum compaction degree equals 2 the height of the electrodes 4a and 4b equals the tripled diameter of the eddy-current sensor winding, that is $h_{pl}=3D_{ec}$. Taking into regard that the maximum capacitance value of the level measuring condenser, as shown by Example 5, equals 6.93 pF, the level measuring sensitivity equals 0.087 pF/mm.

The circuit for measuring the level measuring condenser capacitance is similar to the circuit for measuring the weight measuring condenser capacitance.

After the analog-to-digital conversion the information from the capacity measuring unit outlet of the level capacitor is fed to the sample volume determining unit formed by using a special purpose microprocessor computing device (FIG. 4). In this unit by scale transformation the level calculation is performed and subsequently multiplied by a constant equal to the base surface area of the vessel with the powder.

The compacting process is performed by a series of N sequential pulses. For example, N=10. After each series, measurements are preferably taken of the sample volume and its electrical conductance. Density is calculated by dividing the sample weight by its volume. The values of the powder electrical conductance accompanied by respective density values ($\sigma_i$, $\rho_i$) are fed to the approximation unit. The results of the practical studies of the powders shown in Example 6 demonstrate that output information includes the value of the specific electrical conductance obtained at the maximum compaction of the powder, as well as the slope of the linear dependency between conductance and density.

In the first case the conductance value that is the best characteristic of the powder material itself is obtained, while in the second case, at linear dependencies between the conductance and density that are often observed in experiments, we obtain a parameter that characterizes the given powder irrespective of its density. It is reasonable to use this parameter when powders are compared to each other.

Therefore in the maximum recording unit the electrical conductance value is determined in correspondence to the maximum density; the signal indicating that the maximum density is achieved enters this unit from the outlet of the chain comprised of the gradient calculation unit and threshold comparing unit. The approximation of the value pairs of electrical conductance and density ($\sigma_i$, $\rho_i$) is carried out through a linear relationship in the approximation unit using the least squares method while the inclination angle tangent of the approximating straight line is recorded in the steepness determination unit. The value of electrical conductance accompanied by the value of maximum density, and the value of the inclination angle tangent are shown by the indicator.

The sampler vibration used for powder compacting is effected using an electromagnet with the core 11 and winding 12 (see FIG. 2, as well as springs 10 and a plate 15 made of magnetic metal, that forms the upper base of the spring system.

The electromagnet winding is fed by a series of N current pulses from a pulse series generator (in our case the number of pulses in a series is constant, N=10). The calculation of the vibration electromagnetic system for our concrete case is shown in Example 8.

Synchronization of the sample volume determination unit, electrical conductance determination unit and corrective action forming unit from the pulse generator is effected in such a way that the operations of determining the sample volume, powder electrical conductance and correction are synchronized relative to each other. The sample volume values recorded at time moments $n_i$ enter the gradient calculation unit. Then the gradient values are compared with the threshold, and when they become less than the threshold value it indicates that the powder is not further compacted, the pulse series generator is switched off, and the vibration compaction of the powder ceases.

The functional units of the special-purpose microprocessor computing device (see FIG. 5 can be produced as regards both its hardware and software.

EXAMPLES

The present invention is further illustrated by the following specific examples, which should not be construed as limiting the scope or content of the invention in any way.

Example 1

The magnetic field of a circular coil with current I of radius R is first considered. It is known that the magnetic field intensity on the coil axis, that is at $\rho=0$ is determined by the formula:

$$H_z = \frac{I}{2}\frac{R^2}{[R^2+z^2]^{3/2}}, \quad (11)$$

where $\rho$, z are coordinates of the cylindrical system of coordinates whose center is coincident with the center of the coil. The field intensity in the coil center.

$$H_z(z=0) = \frac{I}{2R}. \quad (12)$$

The relationships $H_z/H_z(z=0)$ as a function of the coordinate z normal to the coil plane is now considered.

The respective values of relative intensity $H_z/H_z(z=0)$ calculated according to formulas (11) and (12) as a function of the rated coordinate z/R are given in Table 1. According to Table 1 the magnetic field intensity at distance z along the coil axis equal to its diameter is 8.9% relative to the intensity value in the coil center.

TABLE 1

| $H_z/H_z(z = 0)$ | z/R |
|---|---|
| 1 | 0 |
| 0.715 | 0.5 |
| 0.354 | 1.0 |
| 0.171 | 1.5 |
| 0.089 | 2.0 |

Example 2

The formula for determining the capacitance per length unit (1 m) between infinitely long cylindrical casings of circular cross-section in case when one of the casings is arranged inside of the other (see FIG. 7) has the following form:

$$C_{l=1m} = \frac{2\pi\varepsilon_0\varepsilon}{\mathrm{Arch}\frac{R_1^2+R_2^2-d^2}{2R_1R_2}}, \quad (13)$$

where l is the coordinate along the cylinder generating line; $\epsilon$ is the dielectric permeability of the material between the cylindrical casings, $R_1$ and $R_2$ are the radiuses of the casings, d is the shift of the casing axes, $\epsilon=8.854*10^{-12}$ F/m is the dielectric constant of free space.

Value Arch x is Expressed as Follows:

$$y=\mathrm{Arch}x=\ln(x-\sqrt{x^2-1}), \text{ for } x\geq 1 \text{ and } -\infty<y\leq 0; \quad (14)$$

$$y=\mathrm{Arch}x=\ln(x+\sqrt{x^2-1}), \text{ for } x\geq 1 \text{ and } 0\leq y\leq\infty. \quad (15)$$

In one case $R_2=12$ mm; $R_1=13.5$ mm+$T_0=14.5$ mm ($T_0$ is the thickness of the casing wall in the area of the outer wafer of the sample weight measuring capacitor $T_0=1$ mm). The outer wafer is arranged in the casing wall recess. The casing wall thickness beyond the recess is 2 mm.

The resultant dielectric permeability of the two-layer capacitor containing a layer of fiberglass laminate of thickness $T_0=1$ mm $\epsilon_g=6$ and an air layer $T=1.5$ mm and $\epsilon=1$ is determined using the following formula:

$$\frac{1}{\epsilon_p} = \frac{\frac{T_0}{\epsilon_g} + \frac{T}{\epsilon}}{T_0 + T}. \tag{16}$$

$\epsilon_p=1.5$ is obtained.

The capacity of the for the capacitor with electrode width of 2 cm is determined by dividing the capacity value $C_{l=1m}$ by 50. Table 2 shows the weight determining condenser capacity values for different shift values d between the axial lines of the cylindrical casings. The expression (14) gives a negative value under the sign ln, therefore expression (15) was used for capacity calculation. The relationship graph $\lambda = C(d)/C(d=0)$ in accordance with the data of Table 2 is given in FIG. 8b.

TABLE 2

| d (mm) | C (pF) | $\lambda = C(d)/C(d=0)$ |
|---|---|---|
| 0 | 8.82 | 1.0 |
| 0.3 | 8.88 | 1.007 |
| 0.6 | 9.07 | 1.029 |
| 0.9 | 9.45 | 1.071 |
| 1.2 | 10.05 | 1.139 |
| 1.5 | 11.01 | 1.248 |

Example 3

Figure 9A:
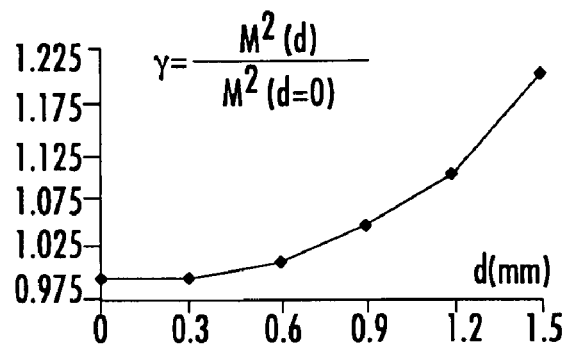
FIG. 9 provides reduced relationships of the square of self-inductance for an eddy-current sensor: a) and capacity of condenser for weight measuring by the shift of the sampler and casing b) axes.
Figure 9B:
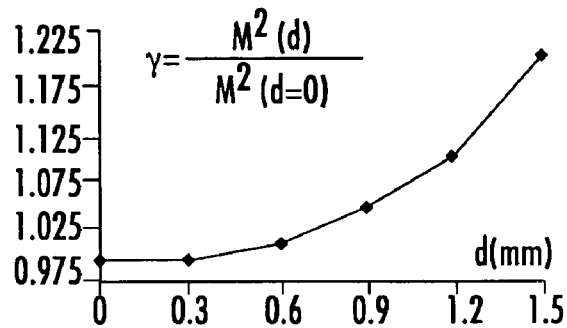
Figure 10:
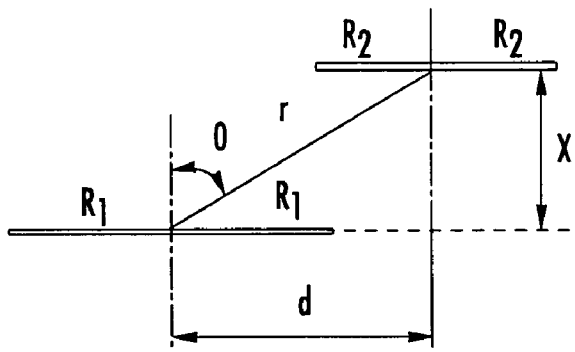
FIG. 10 show relative positions of the circular coils with radiuses $R_1$ and $R_2$.

Two circular circuits with different radii and parallel axes are now considered as shown in FIG. 9. Value x we shall take equal to zero, in this case $\Theta=\pi/2$. The radius of the eddy-current circuit shall be taken equal to the inner sampler radius $R_2=11$ mm. The coil radius of the eddy-current sensor shall be taken equal to the inner radius of casing R plus the thickness of the casing wall in the area of the winding location $T_0$: $R_1=R+T_0=13.5$ mm+1 mm =14.5 mm. It should be noted that beyond the eddy-current sensor winding the thickness of the casing wall equals 2 mm.

In case $d<R_1-R_2=3.5$ mm, the mutual induction can be found by the following formula:

$$M = \pi\mu_0 \frac{R_2^2}{R_1} \sum_{n=0}^{\infty} (-1)^n \frac{(2n+1)!}{2^{2n+1}(n!)^2}\left(\frac{d}{R_1}\right)^{2n} F\left(n+\frac{1}{2}, n+\frac{3}{2}, 2, \frac{R_2^2}{R_1^2}\right) P_{2n}(\cos\Theta), \tag{17}$$

where F is a hyper geometric series, $P_{2n}$ is Legendre's polynom.

The hyper geometric series of the variable x and of the parameters a, b, c is determined by the following formula:

$$F(a,b,c,x) = 1 + \frac{ab}{1 \cdot c}x + \frac{a(a+1)b(b+1)}{1 \cdot 2 \cdot c \cdot (c+1)}x^2 + \frac{a(a+1)(a+2)b(b+1)(b+2)}{1 \cdot 2 \cdot 3 \cdot c(c+1)(c+2)}x^3 + \ldots \tag{18}$$

Table 3 contains the values of the squared mutual induction coefficient M, included in formula (10) at various shift values d.

TABLE 3

| d (mm) | $M^2 \cdot 10^{-14} \Gamma_H$ | $\gamma = M^2(d)/M^2(d=0)$ |
|---|---|---|
| 0 | 0.01345 | 1.0 |
| 0.3 | 0.01345 | 1.0 |
| 0.6 | 0.01369 | 1.018 |
| 0.9 | 0.01416 | 1.053 |
| 1.2 | 0.01488 | 1.1106 |
| 1.5 | 0.01638 | 1.218 |

The Table shows that at the maximum shift d=1.5 mm the linkage coefficient value in formula (10) increases by 21.8%. The relationship graph $\gamma = M^2(d)/M^2(d=0)$ is shown in FIG. 8a, as well as the graph of the relationship between the reduced capacitance of the weight measuring condenser $\gamma = C(d)/C(d=0)$ and the shift d, drawn in accordance with the Table 2 from Example 2 (FIG. 8b).

Example 4

Figure 11A:
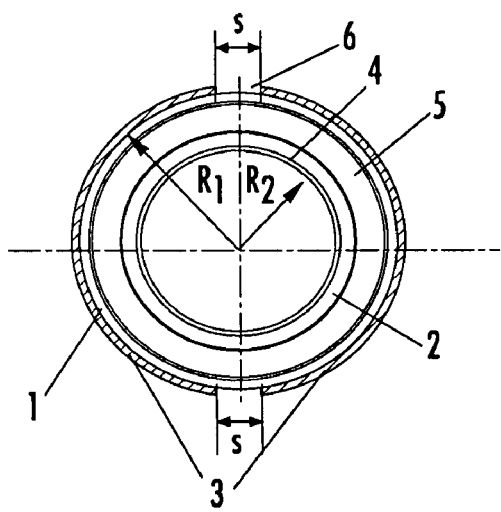
FIG. 11 is a diagram of plate arrangements of the capacitor for measuring the powder level in the sampler (top view)—a) and its plane-parallel approach—b), according to an embodiment of the invention
Figure 11B:
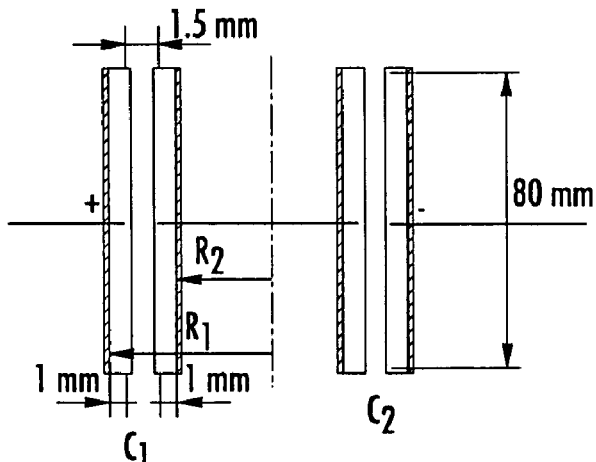
Figure 12:
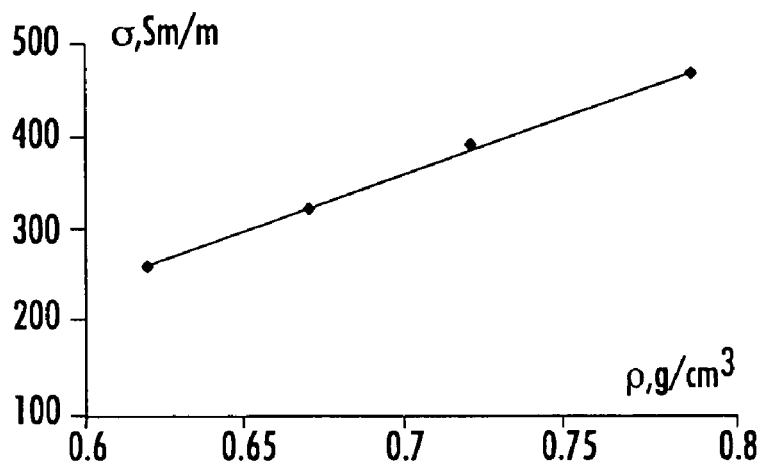
FIG. 12 shows electrical conductance a as a function of density ρ for graphite powder No. 1 obtained using a eddy current measurement apparatus according to an embodiment of the invention.
Figure 13:
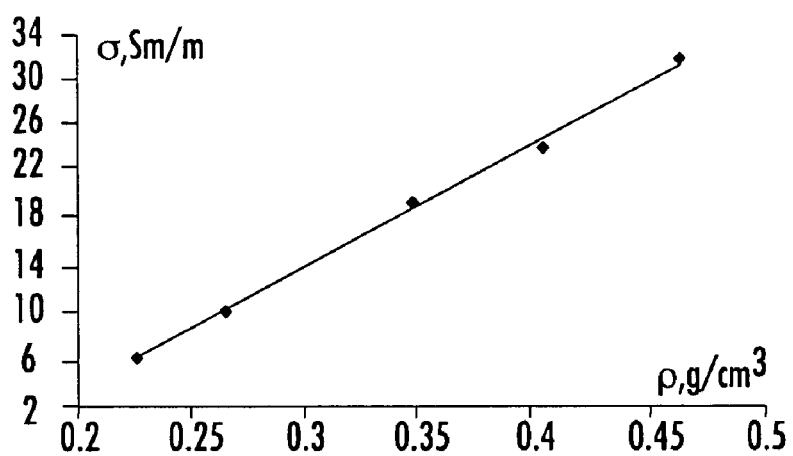
FIG. 13 shows electrical conductance a as a function of density ρ for graphite powder No. 2 obtained using a eddy current measurement apparatus according to an embodiment of the invention.
Figure 14:
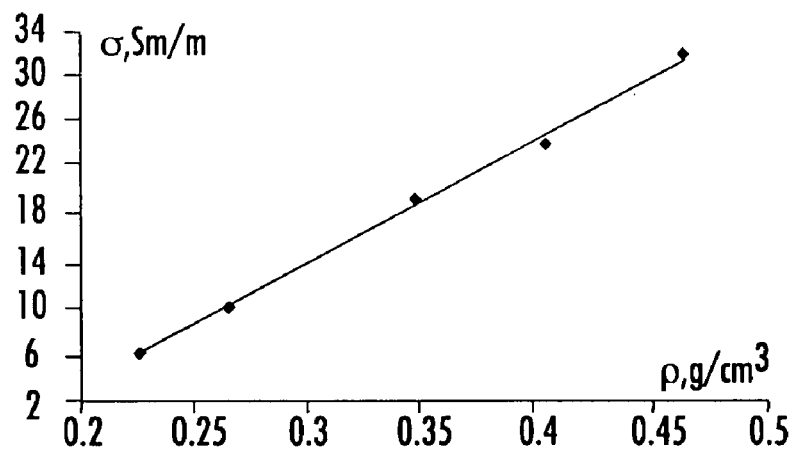
FIG. 14 shows electrical conductance a as a function of density ρ for graphite powder No. 3 obtained using a eddy current measurement apparatus according to an embodiment of the invention.
Figure 15:
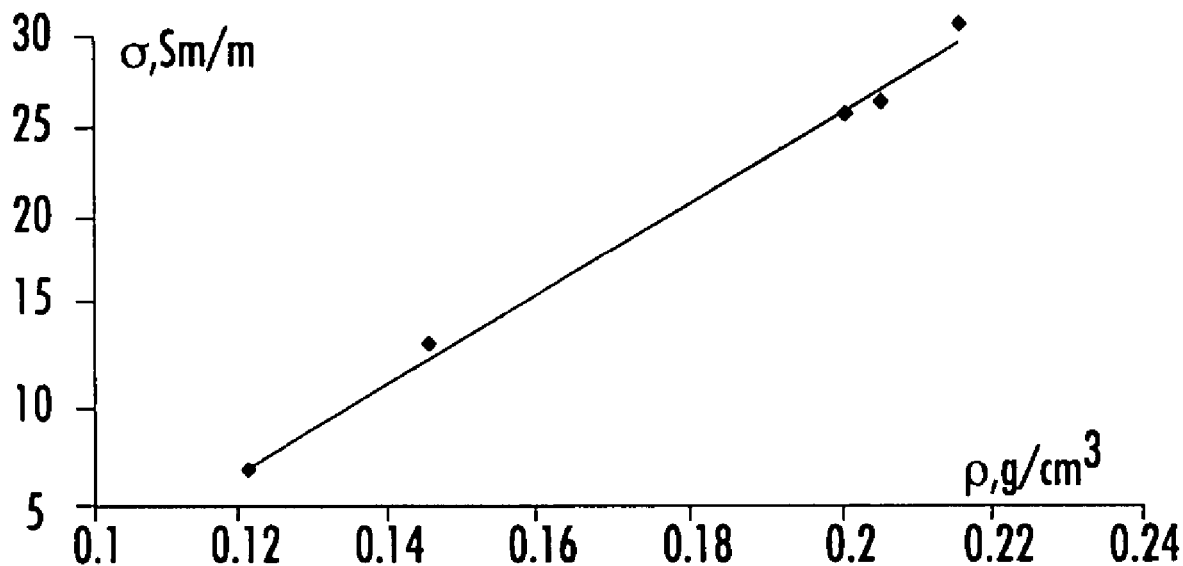
FIG. 15 shows electrical conductance a as a function of density ρ for graphite powder No. 4 obtained using a eddy current measurement apparatus according to an embodiment of the invention.
Figure 16:
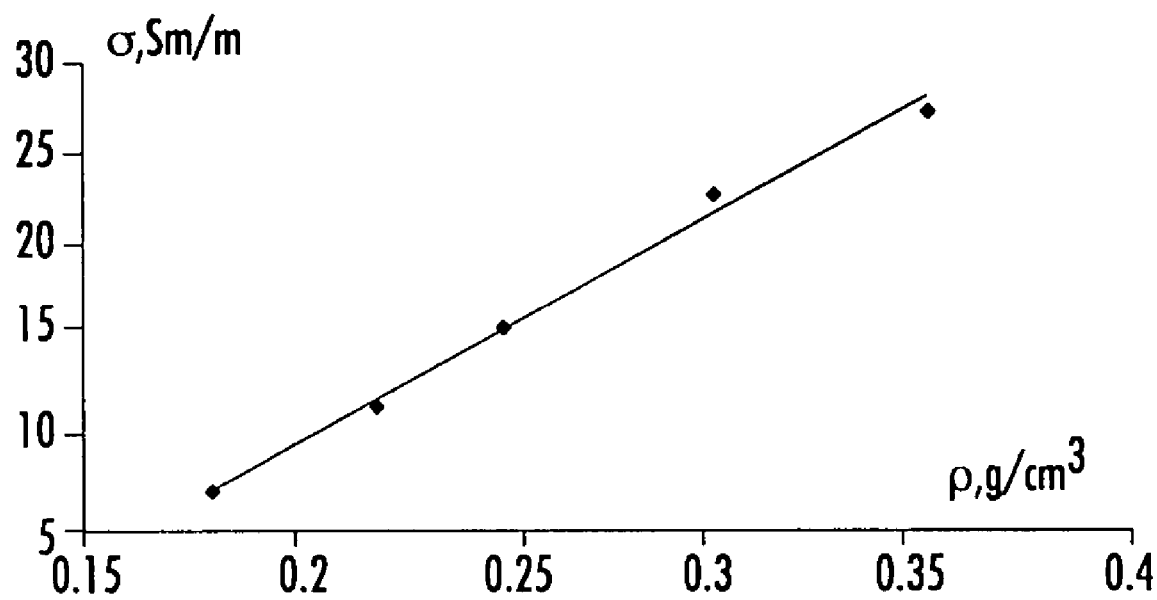
FIG. 16 shows electrical conductance a as a function of density ρ for graphite powder No. 5 obtained using a eddy current measurement apparatus according to an embodiment of the invention.

When the powder is compacted in the sampler by mechanical vibration sampler shifts may occur in the radial direction bounded by the size of the gap between the outer lateral surface of the sampler 1 and the inner lateral surface of the housing 13. FIG. 11 illustrates a schematic arrangement of the linings in the condenser for measuring the powder level in the sampler (top view). Taking into regard that the gap between the sampler 1 and the housing 13 is much less then the length of the electrodes, the cylindrical condensers (FIG. 11) can be presented in the form of two series connected plane-parallel condensers (FIG. 11b).

The radii $R_1$ and $R_2$ in the exemplary case are: $R_1=14.5$ mm, $R_2=11$ mm. The gap between the wafers is $S=5.5$ mm. Then the length of each of the outer electrodes $l_1=40$ mm.

When calculating the length of each inner electrode that collects charges of the opposite sign, it is approximated that the foil areas located opposite of the gaps S do not participate in concentrating the charges have a width $S_1=2.5$ mm each. Then the length of each of the two inner electrodes on the foil $l_2=32$ mm. For the plane-parallel model (FIG. 11b) it is assumed that that the electrode width equals the average value $l_1$ and $l_2$, that is 36 mm. The electrode height of the plane-parallel condenser equals the height of real electrodes arranged on the housing 13, that is 80 mm. Hence the surface area of each electrode of the plane-parallel condenser $S=2.88 \cdot 10^{-3}$ m$^2$.

The reach of the two condensers shown in FIG. 11$^b$ are now considered. Between the condenser liners three layers of a dielectric are arranged: casing wall-air gap-sampler wall, of respective thickness: 1 mm-1.5 mm-1 mm. It is known that the resultant dielectric penetrability of such system is determined in the following manner:

$$\frac{1}{\varepsilon_p} = \frac{\frac{T_1}{\varepsilon_1} + \frac{T_2}{\varepsilon_2} + \frac{T_3}{\varepsilon_3}}{T_1 + T_2 + T_3}, \quad (19)$$

where $T_i$ and $\varepsilon_i$ are the thicknesses and dielectric penetrability of respective layers; $T_1=T_3=1$ mm, $\varepsilon_2=1$.

Value $T_2$ in the initial position when the axial lines of the sampler and the casing coincide is accepted to be 1.5 mm ($T_2=1.5$ mm). The dielectric penetrability of the casing and sampler material is accepted to be 6 ($\varepsilon_1=\varepsilon_3=6$). Fiber-glass laminate has such an $\varepsilon$.
Then $$\varepsilon_p = \frac{3.5\varepsilon_1}{2 + 1.5\varepsilon_1} = 1.91. \quad (20)$$

In such case the capacitances of the condensers C1 and C2 connected in series (FIG. 11$^b$) are equal:

$$C_1 = C_2 = \frac{\varepsilon_p \varepsilon_0 S}{T_1 + T_2 + T_3} = 13.86 \text{ pF} \quad (21)$$

In this case the capacitance of the powder level measuring condenser equals: $C_p=6.93$ pF.

When the sampler axis is shifted leftward by d=0.2 mm for condenser $C_1$ value $T_2=1.3$ mm, for $C_2$-$T_2=1.7$ mm. The dielectric permeability $C_1$ in this case equals: C $\to \varepsilon_p=2.02$; for $C_2 \to \varepsilon_p=1.82$. In such case the condenser capacitance $C_1=15.55$ pF, and condenser capacitance $C_2=12.49$ pF. Then $C_p=6.926$ pF. The $C_p$ values similarly calculated at different shift values d are shown in Table 4.

From the table it follows that the changing of the condenser capacitance for measuring the powder level in the sampler during the shift of the sampler and casing axes does not exceed 0.3%. Hence, the radial oscillations of the sampler practically have no influence on the level measurement results.

TABLE 4

| $C_p$ (pF) | d (mm) |
|---|---|
| 6.93 | 0 |
| 6.926 | 0.2 |
| 6.934 | 0.4 |
| 6.913 | 0.6 |
| 6.917 | 0.8 |
| 6.94 | 1.0 |
| 6.93 | 12 |
| 6.92 | 1.4 |

At the maximum shift d=1.4 mm $C_1=58.67$ pF, and $C_2=7.85$ pF, hence the stabilizing effect is achieved to a significant degree due to the series connection of the condensers $C_1$ and $C_2$.

Example 5

The electrode height of the powder level measuring condenser is now calculated. Taking the winding diameter of the eddy-current sensor D=27 mm it is found that the powder level is limited below by the 27 mm distance from the lowest coil of the winding. The width of the recess for placing the winding also equals 27 mm. The distance between the upper coil of the winding and the lower wafers end face of the level measuring condenser is also 27 mm. The height of the wafers of the level measuring condenser h=80 mm. Thus, the total height of the powder vessel $h_z=161$ mm.

Results from experiments for compacting powders are presented for 5 exemplary powder samples. Initial densities obtained after charging a powder sample into the sampler without compacting were as follows: $\rho_{min}^{(1)}=062$ g/cm$^3$; $\rho_{min}^{(2)}=0.23$ g/cm$^3$; $\rho_{min}^{(3)}=0.26$ g/cm$^3$; $\rho_{min}^{(4)}=0.12$ g/cm$^3$; $\rho_{min}^{(5)}=0.18$ g/cm$^3$. After vibration compacting using a apparatus according to ther invention, the following maximum density values were obtained: $\rho_{max}^{(1)}=0.79$ g/cm$^3$; $\rho_{max}^{(2)}=0.44$ g/cm$^3$; $\rho_{max}^{(3)}=0.48$ g/cm$^3$; $\rho_{max}^{(4)}=0.215$ g/cm$^3$; $\rho_{max}^{(5)}=0.35$ g/cm$^3$.

The respective relationship $\eta=\rho_{max}/\rho_{min}$ is: $\eta_1=1.27$; $\eta_2=1.91$; $\eta_3=1.85$; $\eta_4=1.79$; $\eta_5=1.94$. From the obtained data it follows that the degree of the maximum compacting was found to be limited to a factor of two. This is also observed for other types of the powders that were studied. Considering that the initial height of the powder column in the sampler $h_p=162$ mm it is found that after a two-stage compacting the residual height of the column equals 81 mm.

Hence, at the compaction $\eta_{max}=2$ the lower end face of the cylinder placed on top of the powder is found on the level of the lower end face of the outer electrodes 4$a$ and 4$b$. The maximum capacitance will be reached whose value, according to Table 4, of the previous Example at d=0 equals 6.93 pF.

Example 6

This example shows the results of experimental studies and calculation of the electrical conductivity of five modifications of graphite powders respectively marked by numbers No 1-No 5. The experimental procedure was somewhat simplified in comparison to the proposed invention.

The pass-through eddy-current sensor utilized comprised a cylindrical induction coil directly wound on a dielectric cylindrical sampler containing the powder at hand. The outer coil diameter is 28.7 mm, winding length was 22.7 mm, wound wire diameter 0.4 mm, and number of coils W=48.

Tables 5-9 show the values of the relative added active resistance of the eddy current sensor $r_{ad}/\omega L_0$ as a function of powder density p, measured at frequency f=2 MHz. Compacting was carried out by mechanical vibration of the sampler.

Relationships between the sensor added resistance and density.

TABLE 5

Sample No 1.

| $\rho$, g/cm$^3$ | $r_{ad}/\omega L_0 \cdot 10^{-3}$ |
|---|---|
| 0.62 | 74.5 |
| 0.67 | 87.7 |
| 0.72 | 107.8 |
| 0.79 | 125.3 |

TABLE 6

Sample No 2.

| ρ, g/cm³ | $r_{ad}/\omega L_0 \cdot 10^{-3}$ |
|---|---|
| 0.23 | 2.57 |
| 0.26 | 3.32 |
| 0.34 | 5.8 |
| 0.40 | 7.84 |
| 0.44 | 9.51 |

TABLE 7

Sample No 3.

| ρ, g/cm³ | $r_{ad}/\omega L_0 \cdot 10^{-3}$ |
|---|---|
| 0.26 | 2.59 |
| 0.30 | 4.37 |
| 0.35 | 4.87 |
| 0.45 | 7.59 |
| 0.48 | 9.79 |

TABLE 8

Sample No 4.

| ρ, g/cm³ | $r_{ad}/\omega L_0 \cdot 10^{-3}$ |
|---|---|
| 0.12 | 2.63 |
| 0.145 | 3.87 |
| 0.20 | 7.34 |
| 0.205 | 7.87 |
| 0.215 | 8.27 |

TABLE 9

Sample No 5.

| ρ, g/cm³ | $r_{ad}/\omega L_0 \cdot 10^{-3}$ |
|---|---|
| 0.18 | 2.76 |
| 0.22 | 3.52 |
| 0.25 | 4.81 |
| 0.30 | 6.44 |
| 0.35 | 8.01 |

Presenting the tabulated data in the form of relationships between $r_{ad}/\omega L_0$ and density linearity can be seen.

The electrical conductivity of the graphite powder samples is now calculated at different densities. The electromotive force of the outer pass-through eddy-current sensor with a uniform field in the testing zone is determined by the following formula:

$$\dot{E} = -j\pi\mu_0 \omega W \dot{H}_0 R^2 (1 - \eta + \eta \mu_r \mu_{3\Phi\Phi}) \quad (22)$$

where $\dot{H}_0$ is the magnetic field intensity in the testing zone when the test object is absent (for a coil in the form of a long solenoid), ω—frequency, W—number of solenoid coils, R—solenoid radius, $\mu_r$—relative magnetic permeability of the control object, $_{3}\Phi\Phi$—effective magnetic permeability determining the magnetic stream weakening degree due to eddy currents, η—filling coefficient determined as a relation of the relationship of the cross-section surface areas of the testing object and the magnetic field pipe connected to the sensor winding.

The relative input e.m.f. rated against the initial e.m.f.:

$$\dot{E}_{ad^*} = -j\eta(\mu_r \mu_{3\phi\phi} - 1), \quad (23)$$

where $\mu_{3\phi\phi} = \dfrac{2I_1(x)}{xI_0(x)}, \quad (24)$ $I_1(x)$ and $I_0(x)$ are modified Bessel's functions (cylindrical functions) of grade one, respectively of the first and zero order, $x = \sqrt{-j\omega\mu_r\mu_0\sigma}$, σ—specific electrical conductivity of the control object.

The value of the added impedance rated against the initial inductive reactance $$z_{ad^*} = \dfrac{z_{ad}}{\omega L_0} = -\dot{E}_{ad^*}. \quad (25)$$

The tables of the actual and imaginary parts $\mu_{3\Phi\Phi}$, correspondingly $R_e \, \mu_{3\Phi\Phi} \cdot 10^{-6}$ and $-I_m \, \mu_{3\Phi\Phi} \cdot 10^{-6}$ as a function of the generalized parameter value $\beta = R\sqrt{\omega\sigma\mu_0}$ are known. These tables and values of the active added resistance given above in Tables 5-9 were used for calculating the electrical conductivity values σ of powders (samples 1-5) at various densities ρ. The corresponding relationships are shown in FIGS. 12-16

The most typical feature of the graphs shown is the linearity of the electrical conductivity—density relationship. Thus the steepness of these graphs reflected by the tangent of the inclination angle does not depend on the density and may serve as an integral characteristic of a powder-like material. Table 10 shows the values of the inclination angle tangents tgφ for the studied graphite powders in accordance with FIGS. 12-16

TABLE 10

| Sample No | tgφ, Sm · sm³/m · g |
|---|---|
| 1 | 1188 |
| 2 | 123 |
| 3 | 125 |
| 4 | 239 |
| 5 | 115 |

Example 7

The Example shows the results of conventional contact measurements on the same powder-like graphite samples obtained using the invention as described in example 6 using an alternating current (f=1 kHz) and a direct current. 15 mm diameter round copper alloy electrodes were used, with the distance between the electrodes being 18.5 mm. The working surfaces of the electrodes were ground.

The AC measurements will be described first. The obtained relationships between the electrical conductivity σ and density ρ are mostly of non-monotonous character. For sample No 1 with the density increase initially a drop of σ=10.2 Sm/m (at ρ=0.54 g/cm³) to 9.6 Sm/m (at ρ=0.66 g/cm³) is observed, whereafter the value a gets increased. It should be noted that the here obtained value a at the maximum density (σ=28 Sm/m at ρ=0.77 g/cm³) is approximately 16 times less than the value σ, obtained with the eddy-current method according to the invention.

The explanation may lie in the structure of the powder particles. For sample No. 1 they are in the form of "fish-scales" of 2-3 mm² surface area, about 100 μm thick. The surface layer of the "scales" is harder in comparison to the material within their volume.

Also, this layer seems to have a higher resistance, hence it increases the contact resistances between the powder particles and the surface of the electrodes, thus reducing the pass-through conductivity.

For eddy currents the presence of the high-resistance surface layer in the powder particles is not so critical since the eddy currents for closed trajectories within the particles. For sample No 2 with the increase of ρ a deep drop of σ is observed, from σ=3.52 Sm/m at ρ=0,21 g/cm³ to σ=0.69 Sm/m at ρ=0.32 g/cm³, with a subsequence growth of σ to 15,4 Sm/m at ρ=0.35 g/cm³. A similar form have the relationships σ(ρ) for samples No 3 and No 4. The relationship σ(ρ) for sample No 5 is generally characterized by two bending points.

The contact measurements demonstrated a high instability. A minute change in the powder density leads to a substantial change of the results. After a powder compacting procedure there was often observed a transition process of up to 10 minutes duration, while the conductivity increased in this case by about 40%.

A post-compaction conductivity increase may be related to the change in the position of powder particles within the volume and at the surface of the electrodes. Any transition processes in the conductivity determination have not been observed during the non-contact measurements. This phenomenon seems to mainly characterize the degree of the contact between the electrodes and the particulate material while the integral contact resistance on the surface of the electrodes gets reduced during the time of the transition process. Below are the results of measurements using direct current.

In the characteristic σ(ρ) for the sample No 1 the descending portion is absent while the dependence monotonously increases. For samples No 2 and No 3 the descending portions are actually specified by one of the six points on the characteristics. For sample No 4 the descending portion is characterized by three points. The dependence σ(ρ) for sample No 5 is manly monotonously increasing. Each point on the described graphs σ(ρ) was obtained by averaging, for which from 5 to 28 measurements were performed.

The transition process during the measurements on the direct current was observed less frequently and was shorter: 1-2 minutes. The instability of the indications at lower density fluctuations remains substantial.

Table 11 allows to quantitatively evaluate the fluctuation level since it contains the root-mean-square deviation values S and the relative root-mean-square errors $S/\sigma_{av}$ during the electrical conductivity change a of sample No 5. In Table 11 the value of N is the number of measurements.

TABLE 11

| ρ, g/cm³ | N | $\sigma_{av}$, Sm/m | S, Sm/m | $S/\sigma_{av}$, % |
|---|---|---|---|---|
| 0.16 | 14 | 2.44 | 0.89 | 36 |
| 0.18 | 14 | 3.79 | 1.69 | 45 |
| 0.22 | 21 | 7.36 | 1.85 | 25 |
| 0.23 | 28 | 10.06 | 2.36 | 23.5 |
| 0.25 | 28 | 9.67 | 2.15 | 22 |

As follows from Table 11, the relative root-mean-square error $S/\sigma_{av}$ gets lower with the density increase, but it does not get lower than by 22%.

The non-contact eddy-current measurements, as follows from the graphs shown in FIGS. 11-15, feature a much lower error.

Example 8

The calculations regarding the electromagnet for the vibration system are now described. The selected material permeability of the magnetic wafer μ, that is attracted to the electromagnet poles equals μ=2000. This corresponds to the i value of the metallic wafers used as a transformer core.

The wafer attraction force is calculated according to the known formula that is valid for electromagnets with a Π—shaped core:

$$|F| = \frac{S}{\mu_0}\left(\frac{\mu\mu_0 NI}{l+2\mu x}\right)^2, \quad (26)$$

where S is the contact area between the core and the wafer (armature), N—number of winding coils, l—length of magnetic circuit, I—current in the winding, x—gap value between the armature and the electromagnet poles.

The average current density in the winding of small transformers can be accepted to be equal $I_{av}$=2 A/mm². If the winding wire thickness $d_0$=0.5 mm then the current in the electromagnet winding equals I=0.4 A. The core section is 7×7 mm. In our case the total length of the magnetic circuit l=2·35+23=93 mm. The winding length is 27 mm. The number of coils in one winding layer $N_1$=50. The number of layers in each winding n=8. Hence, the total number of coils in two windings of a Π—shaped core N equals N=800. Let us specify the gap value x=5 mm. Substituting these data into formula (26), we obtain that F=0.1248 H.

If the second Π—shaped core with an identical winding is arranged perpendicularly to the first one so that the first and the second cores have a common symmetry axis, we obtain a doubled attraction force: $F_\Sigma$≈0,25 H. In such case the spring is centrally positioned between the electromagnet poles.

As it was stated above, the weight of the powder charged into the sampler P=40 g causes a downward shift of the sampler by $\Delta x_m$=20 mm. In this case the assumed initial (without compacting) powder density ρ=0.7 g/cm³. If the assumed initial density $\rho_{min}$=0.12 g/cm³ (see Table 8), then the sampler will shift by $\Delta x_1$=3.4 mm; naturally, the spring will be compressed by the same value. Then, in order to have the spring further compressed by $\Delta x_2$=20−3,4−5=11.6 mm a force F=0.23 H will be required. Thus, by lowering the sampler with the given powder to the level at which the distance between the magnetic wafer structurally linked by a fixing mechanism to the sampler bottom and the electromagnet poles gets equal to 5 mm we turn on the vibration mechanism because the magnet attractive force gets higher of the wafer elastic force. With the reduction of the distance between the magnetic wafer and the poles the attraction force increases faster than the spring elastic force because the latter increases proportionally to the shift, while the attraction force in accordance with (26) is inversely proportional to the squared gap value, the first addend in the denominator (26) is much less than the second one. By reducing the current amplitude of the pulses fed to the electromagnet winding it is possible to regulate the attraction force, and, respectively, the vibration intensity.

While various embodiments of the present invention have been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A method for non-contact measurement of electrical conductivity of powder-like materials using eddy currents, comprising the steps of:
   placing a powder to be measured in a sampling container comprising a hollow dielectric material, said sampling container disposed and freely axially moving within an outer dielectric housing, wherein an eddy-current sensor comprising a winding is arranged on an outside surface of said housing;
   forcing current in said winding to excite said powder to generate eddy currents;
   measuring an introduced active resistance detected at said eddy-current sensor,
   determining an electrical conductivity of said powder using said active resistance,
   measuring a density of said powder, and
   vibration compacting of said powder, wherein during said vibration compacting step, said determining electrical conductivity step and said measuring said density step is repeated at a plurality of stages.

2. The method of claim 1, further comprising the step of determining an axial movement of said sampling container relative to said housing, and correcting said active resistance for said axial movement.

3. The method of claim 2, wherein said axial movement is determined using a capacitive measurement.

4. The method of claim 1, wherein said vibration compacting step comprises powering an electromagnet disposed under a bottom of said sampling container using a series of current pulses.

5. The method of claim 4, further comprising the step of disposing a hollow thin-walled dielectric cylinder whose lateral surface includes an electrically conductive layer thereon inside said sampling container on top of said powder.

6. The method of claim 5, further comprising the step of measuring a level of said powder in said sampling container during said vibration compacting step based on a capacitance between a pair of spaced apart electrical conductors disposed on an outer surface of said housing and said electrically conductive layer on said thin-walled dielectric cylinder.

7. The method of claim 1, wherein a minimum bulk density and a maximum bulk density are determined during said vibration compacting step, further comprising the step of determining frequency band limits for an operating frequency of said eddy current sensor using said minimum bulk density and said maximum bulk density, and determining said operating frequency within said band limits according to a maximum Q-factor of said eddy current sensor.

8. An eddy current sensing apparatus for non-contact measurement of electrical conductivity of powder-like materials, comprising:
   an outer dielectric housing, said housing having at least a first pair of electrically isolated electrically conductive wafers disposed on a lower outer surface thereof and a second pair of electrically isolated electrically conductive wafers disposed on a upper outer surface thereof;
   a sampling container comprising a hollow dielectric material for holding a powder sample to be measured, said sampling container having a continuous electrically conductive layer disposed on an outside surface of a lower portion thereof, said sampling container being disposed within and freely axially moving within said housing;
   a hollow dielectric mass, a lateral surface of said dielectric mass having an electrically conductive coating thereon, said dielectric mass disposed inside said sampling container on said powder sample;
   an eddy-current sensor comprising a winding arranged on an outside surface of said housing between said first pair of electrically isolated electrically conductive wafers and said second pair of electrically isolated electrically conductive wafers, and
   a power supply for forcing current in said winding to excite said powder sample to generate eddy currents which are detected and measured as introduced active resistance by said eddy-current sensor,
   wherein said first pair of electrically isolated electrically conductive wafers together with said continuous electrically conductive layer disposed on an outside surface of said sampling container provides capacitance data for determining a weight of said powder sample, and said second first pair of electrically isolated electrically conductive wafers together with said electrically conductive coating on said dielectric mass thereon provides capacitance data for measuring a powder level of said powder sample.

9. The apparatus of claim 8, further comprising a vibration device for compacting said powder sample.

10. The apparatus of claim 9, wherein said vibration device for compacting comprises an a flask including an electromagnet, and a system of springs whose upper base is comprised of a magnetic wafer affixed to said springs, wherein a bottom of said flask is placed on said magnetic wafer, a mechanism for fixing the flask bottom on said magnetic wafer, and a current pulse series generator that powers said electromagnet, wherein said springs attach to a bottom of said sampling container.

11. The apparatus of claim 10, wherein said system of springs provides a weight of said powder, wherein said continuous electrically conductive layer disposed on an outside surface of a lower portion of said sampling container is galvanically linked with said system of springs.

12. A method for non-contact measurement of electrical conductivity of powder-like materials using eddy currents, comprising the steps of:
   placing a powder to be measured in a sampling container comprising a hollow dielectric material, said sampling container disposed and freely axially moving within an outer dielectric housing, wherein an eddy-current sensor comprising a winding is arranged on an outside surface of said housing;
   forcing current in said winding to excite said powder to generate eddy currents;
   measuring an introduced active resistance detected at said eddy-current sensor;
   determining an electrical conductivity of said powder using said active resistance, and
   determining an axial movement of said sampling container relative to said housing, and correcting said active resistance for said axial movement.

* * * * *